(12) United States Patent
Burgess et al.

(10) Patent No.: US 6,699,967 B1
(45) Date of Patent: Mar. 2, 2004

(54) HEPATOMA-DERIVED GROWTH FACTOR-LIKE PROTEINS, POLYNUCLEOTIDES ENCODING THEM AND METHODS OF USE

(75) Inventors: Catherine Burgess, Wethersfield, CT (US); Richard A. Shimkets, West Haven, CT (US); Corine Vernet, North Branford, CT (US); Ferenc L. Boldog, North Haven, CT (US); Meiji Yang, East Lyme, CT (US); William J. La Rochell, Madison, CT (US); Stacey Minskoff, Stamford, CT (US)

(73) Assignee: CuraGen Corporation, New Haven, CT (US)

( * ) Notice: Subject to any disclaimer, the term of this patent is extended or adjusted under 35 U.S.C. 154(b) by 185 days.

(21) Appl. No.: 09/675,016

(22) Filed: Sep. 28, 2000

Related U.S. Application Data
(60) Provisional application No. 60/156,975, filed on Oct. 1, 1999.

(51) Int. Cl.[7] .............................................. C07K 14/00
(52) U.S. Cl. ........................................... 530/350; 514/2
(58) Field of Search ............................... 530/350, 412; 514/2

(56) References Cited

FOREIGN PATENT DOCUMENTS

| WO | WO 96/39485 | 12/1996 |
| WO | WO 98/24901 | 6/1998 |

OTHER PUBLICATIONS

Nakamura, et al., 1994, J. Biol. chem,, 264(40):25143–49.*
Burgess et al., J of Cell Bio. 111:2129–2138, 1990.*
Lazar et al. Molecular and Cellular Biology 8:1247–1252, 1988.*
Bowie et al. Science, 247:1306–1310, 1990.*
Mashreghi–Mohammadi, M. (Nov. 13, 1998). Database EMBL Online Acc. No. AL033539. "Human DNA sequence from clone RP1–309H15 on chromosome 6p22.1–22.3 Contains a gene similar to HDGF (hepatoma–derived growth factor (high–mobility group protein 1–like)). ESTs, STSs, GSSs and a CpG Island." Direct Submission.
Davies, K.E. et al. (Aug. 10, 1995). Database NAGENESEQ Online Acc. No. Q79643. "Longest observed allele of the GCC repeat region in the FRAXE region." PCT Publication WO 94/28172.
International Search Report, issued Aug. 13, 2001.
Dietz, et al., 1999 "HRP–4: A new member of the hepatoma derived growth factor related protein family interacts with HDGF and another HDGF related polypeptide." Unpublished. GenBank Accession No.: CAB40348.
Nakamura, et al., 1994 "Molecular cloning of complementary DNA for a novel human hepatoma–derived growth factor. Its homology with high mobility group–1 protein." *J. Biol. Chem.* 269 (40): 25143–25149. GenBank Accession No.: P51858.
Nakamura, et al., 1994 "Molecular cloning of complementary DNA for a novel human hepatoma–derived growth factor. Its homology with high mobility group–1 protein." *J. Biol. Chem.* 269 (40):25143–25149.

* cited by examiner

*Primary Examiner*—Larry R. Helms
(74) *Attorney, Agent, or Firm*—Ivor R. Elrifi; Naomi S. Biswas; Mintz Levin Cohn Ferris Glovsky & Popeo, PC

(57) ABSTRACT

The present invention provides HDGFX, a novel isolated polypeptide, as well as a polynucleotide encoding HDGFX and antibodies that immunospecifically bind to HDGFX or any derivative, variant, mutant, or fragment of the HDGFX polypeptide, polynucleotide or antibody. The invention additionally provides methods in which the HDGFX polypeptide, polynucleotide and antibody are used in detection and treatment of a broad range of pathological states, as well as to other uses.

6 Claims, 4 Drawing Sheets

SEQUENCE LISTING

```
<160> NUMBER OF SEQ ID NOS: 22

<210> SEQ ID NO 1
<211> LENGTH: 880
<212> TYPE: DNA
<213> ORGANISM: Homo sapiens
<220> FEATURE:
<221> NAME/KEY: CDS
<222> LOCATION: (79)..(831)

<400> SEQUENCE: 1
gcagccgccc ttactgcgcg cgcgcagact tcggcgtcta cttccggtgt ggcccaggcg         60
gggtccgcag aaccagct atg tcg gcc tac ggc atg ccc atg tac aag agc         111
                    Met Ser Ala Tyr Gly Met Pro Met Tyr Lys Ser
                     1               5                   10 ggg gac ctg gtg ttt gcc aag tta aag ggc tat gcc cac tgg ccg gcg         159
Gly Asp Leu Val Phe Ala Lys Leu Lys Gly Tyr Ala His Trp Pro Ala
             15                  20                  25 agg ata gag cac atg acc cag ccc aac cgc tac cag gtg ttt ttc ttc         207
Arg Ile Glu His Met Thr Gln Pro Asn Arg Tyr Gln Val Phe Phe Phe
         30                  35                  40 ggg acc cac gag acg gcc ttc ctg agt ccc aaa cgc ctg ttc ccg tac         255
Gly Thr His Glu Thr Ala Phe Leu Ser Pro Lys Arg Leu Phe Pro Tyr
```

-continued

|   |   |   |   |   |   |   |   |   |   |   |   |   |   |   |   |     |
|---|---|---|---|---|---|---|---|---|---|---|---|---|---|---|---|-----|
|   |   |   |   |   | 45|   |   |   |   | 50|   |   |   |   | 55|     |
| aag | gag | tgc | aag | gag | aag | ttc | ggc | aag | ccc | aac | aag | agg | cgc | ggc | ttc | 303 |
| Lys | Glu | Cys | Lys | Glu | Lys | Phe | Gly | Lys | Pro | Asn | Lys | Arg | Arg | Gly | Phe |     |
| 60  |     |     |     |     | 65  |     |     |     |     | 70  |     |     |     |     | 75  |     |
| agc | gcg | ggg | ctg | tgg | gaa | atc | gag | aac | aac | ccc | acg | gtc | cag | gcc | tcc | 351 |
| Ser | Ala | Gly | Leu | Trp | Glu | Ile | Glu | Asn | Asn | Pro | Thr | Val | Gln | Ala | Ser |     |
|     |     |     |     | 80  |     |     |     |     | 85  |     |     |     |     | 90  |     |     |
| gac | tgc | cca | tta | gcc | tca | gag | aag | ggc | agc | gga | gac | ggg | cct | tgg | ccg | 399 |
| Asp | Cys | Pro | Leu | Ala | Ser | Glu | Lys | Gly | Ser | Gly | Asp | Gly | Pro | Trp | Pro |     |
|     |     |     | 95  |     |     |     |     | 100 |     |     |     |     | 105 |     |     |     |
| gag | ccc | gag | gcc | gca | gag | ggc | gac | gag | gac | aag | ccg | acc | cac | gct | ggt | 447 |
| Glu | Pro | Glu | Ala | Ala | Glu | Gly | Asp | Glu | Asp | Lys | Pro | Thr | His | Ala | Gly |     |
|     |     | 110 |     |     |     |     | 115 |     |     |     |     | 120 |     |     |     |     |
| ggc | ggc | ggc | gac | gaa | ttg | ggg | aag | ccg | gac | gac | gac | aag | ccc | act | gag | 495 |
| Gly | Gly | Gly | Asp | Glu | Leu | Gly | Lys | Pro | Asp | Asp | Asp | Lys | Pro | Thr | Glu |     |
|     | 125 |     |     |     |     | 130 |     |     |     |     | 135 |     |     |     |     |     |
| gag | gag | aag | ggg | ccg | ctg | aag | agg | agc | gcg | ggg | gac | ccg | ccg | gag | gac | 543 |
| Glu | Glu | Lys | Gly | Pro | Leu | Lys | Arg | Ser | Ala | Gly | Asp | Pro | Pro | Glu | Asp |     |
| 140 |     |     |     | 145 |     |     |     |     | 150 |     |     |     |     | 155 |     |     |
| gcc | ccc | aaa | cga | ccc | aag | gag | gca | gcc | ccc | gac | caa | gag | gag | gag | gcg | 591 |
| Ala | Pro | Lys | Arg | Pro | Lys | Glu | Ala | Ala | Pro | Asp | Gln | Glu | Glu | Glu | Ala |     |
|     |     |     | 160 |     |     |     |     | 165 |     |     |     |     | 170 |     |     |     |
| gag | gcg | gag | agg | gcg | gcg | gaa | gcg | gag | agg | gcg | gcg | gcg | gcg | gcg | gcg | 639 |
| Glu | Ala | Glu | Arg | Ala | Ala | Glu | Ala | Glu | Arg | Ala | Ala | Ala | Ala | Ala | Ala |     |
|     | 175 |     |     |     |     | 180 |     |     |     |     | 185 |     |     |     |     |     |
| gcg | acg | gcc | gtc | gac | gag | gag | agt | ccg | ttc | ctc | gtg | gcg | gtg | gag | aac | 687 |
| Ala | Thr | Ala | Val | Asp | Glu | Glu | Ser | Pro | Phe | Leu | Val | Ala | Val | Glu | Asn |     |
|     | 190 |     |     |     |     | 195 |     |     |     |     | 200 |     |     |     |     |     |
| ggc | agc | gcc | cct | agc | gag | ccg | ggc | ctg | gtc | tgc | gag | ccg | cct | cag | cca | 735 |
| Gly | Ser | Ala | Pro | Ser | Glu | Pro | Gly | Leu | Val | Cys | Glu | Pro | Pro | Gln | Pro |     |
|     | 205 |     |     |     |     | 210 |     |     |     |     | 215 |     |     |     |     |     |
| gag | gag | gag | gag | ctc | cgg | gag | gaa | gaa | gtc | gcg | gac | gag | gag | gcc | tcc | 783 |
| Glu | Glu | Glu | Glu | Leu | Arg | Glu | Glu | Glu | Val | Ala | Asp | Glu | Glu | Ala | Ser |     |
| 220 |     |     |     | 225 |     |     |     |     | 230 |     |     |     |     | 235 |     |     |
| cag | gag | tgg | cat | gcc | gag | gca | ccg | ggc | ggc | gga | gat | cgc | gac | agc | ctg | 831 |
| Gln | Glu | Trp | His | Ala | Glu | Ala | Pro | Gly | Gly | Gly | Asp | Arg | Asp | Ser | Leu |     |
|     |     |     | 240 |     |     |     |     | 245 |     |     |     |     | 250 |     |     |     | tagttaccag cgtttccaga agagcccctg ccccgttcct gctgcggcc    880

<210> SEQ ID NO 2
<211> LENGTH: 251
<212> TYPE: PRT
<213> ORGANISM: Homo sapiens

<400> SEQUENCE: 2

Met Ser Ala Tyr Gly Met Pro Met Tyr Lys Ser Gly Asp Leu Val Phe
 1               5                  10                  15

Ala Lys Leu Lys Gly Tyr Ala His Trp Pro Ala Arg Ile Glu His Met
                20                  25                  30

Thr Gln Pro Asn Arg Tyr Gln Val Phe Phe Gly Thr His Glu Thr
            35                  40                  45

Ala Phe Leu Ser Pro Lys Arg Leu Phe Pro Tyr Lys Glu Cys Lys Glu
        50                  55                  60

Lys Phe Gly Lys Pro Asn Lys Arg Arg Gly Phe Ser Ala Gly Leu Trp
 65                  70                  75                  80

Glu Ile Glu Asn Asn Pro Thr Val Gln Ala Ser Asp Cys Pro Leu Ala
                85                  90                  95

Ser Glu Lys Gly Ser Gly Asp Gly Pro Trp Pro Glu Pro Glu Ala Ala

```
                100               105                 110
Glu Gly Asp Glu Asp Lys Pro Thr His Ala Gly Gly Gly Asp Glu
            115                 120                 125
Leu Gly Lys Pro Asp Asp Lys Pro Thr Glu Glu Lys Gly Pro
    130                 135                 140
Leu Lys Arg Ser Ala Gly Asp Pro Pro Glu Asp Ala Pro Lys Arg Pro
145                 150                 155                 160
Lys Glu Ala Ala Pro Asp Gln Glu Glu Ala Glu Ala Glu Arg Ala
                165                 170                 175
Ala Glu Ala Glu Arg Ala Ala Ala Ala Ala Thr Ala Val Asp
                180                 185                 190
Glu Glu Ser Pro Phe Leu Val Ala Val Glu Asn Gly Ser Ala Pro Ser
            195                 200                 205
Glu Pro Gly Leu Val Cys Glu Pro Pro Gln Pro Glu Glu Glu Leu
        210                 215                 220
Arg Glu Glu Glu Val Ala Asp Glu Glu Ala Ser Gln Glu Trp His Ala
225                 230                 235                 240
Glu Ala Pro Gly Gly Gly Asp Arg Asp Ser Leu
                245                 250
```

```
<210> SEQ ID NO 3
<211> LENGTH: 223
<212> TYPE: PRT
<213> ORGANISM: Bos taurus

<400> SEQUENCE: 3

Met Ser Arg Phe Tyr Arg Arg Lys Tyr Lys Cys Gly Asp Leu Val Phe
  1               5                  10                  15
Ala Lys Leu Lys Gly Tyr Ala His Trp Pro Ala Arg Ile Glu Gln Thr
                 20                  25                  30
Ala Glu Ala Asn Arg Tyr Gln Val Phe Phe Gly Thr His Glu Thr
                 35                  40                  45
Ala Phe Leu Gly Pro Arg His Leu Phe Pro Tyr Glu Glu Ser Lys Glu
     50                  55                  60
Lys Phe Gly Lys Pro Asn Lys Arg Arg Gly Phe Ser Glu Gly Leu Trp
 65                  70                  75                  80
Glu Ile Glu Asn Asn Pro Thr Val Gln Ala Ser Asp Tyr Gln Cys Ala
                 85                  90                  95
Leu Glu Lys Ser Cys Pro Glu Glu Pro Glu Pro Glu Val Ala Glu Gly
                100                 105                 110
Gly Glu Asp Pro Lys Ser His Thr Asn Gly Gly Asp Asp Asp Gln
            115                 120                 125
Gly Lys Leu Gly Val Asp Leu Pro Ala Glu Glu Asn Lys Lys Glu
    130                 135                 140
Thr Leu Lys Arg Thr Ala Glu Asp Pro Pro Glu Asp Ile Pro Lys Arg
145                 150                 155                 160
Pro Lys Glu Ala Asp Pro Glu Glu Gly Glu Arg Lys Glu Ala Ala
                165                 170                 175
Ala Val Ala Glu Glu Ala Glu Asp Ala Arg Pro Leu Leu Val Glu Val
                180                 185                 190
Glu Asn Asp Pro Ala Ala Ser Val Leu Gly Leu Ala Trp Gly Leu Pro
            195                 200                 205
Val Met Glu Gln Glu Pro Glu Glu Ser Ala Glu Arg Glu Ala
    210                 215                 220
```

```
<210> SEQ ID NO 4
<211> LENGTH: 221
<212> TYPE: PRT
<213> ORGANISM: Homo sapiens

<400> SEQUENCE: 4

Tyr Lys Cys Gly Asp Leu Val Phe Ala Lys Met Lys Gly Tyr Pro His
  1               5                  10                  15

Trp Pro Ala Arg Ile Asp Glu Met Pro Glu Ala Ala Val Lys Ser Thr
             20                  25                  30

Ala Asn Lys Tyr Gln Val Phe Phe Gly Thr His Glu Thr Ala Phe
         35                  40                  45

Leu Gly Pro Lys Asp Leu Phe Pro Tyr Glu Glu Ser Lys Glu Lys Phe
     50                  55                  60

Gly Lys Pro Asn Lys Arg Lys Gly Phe Ser Glu Gly Leu Trp Glu Ile
 65                  70                  75                  80

Glu Asn Asn Pro Thr Val Lys Ala Ser Gly Tyr Gln Ser Ser Gln Lys
                 85                  90                  95

Lys Ser Cys Val Glu Glu Pro Glu Pro Glu Pro Glu Ala Ala Glu Gly
            100                 105                 110

Asp Gly Asp Lys Lys Gly Asn Ala Glu Gly Ser Ser Asp Glu Glu Gly
        115                 120                 125

Lys Leu Val Ile Asp Glu Pro Ala Lys Glu Lys Asn Glu Lys Gly Ala
    130                 135                 140

Leu Lys Arg Arg Ala Gly Asp Leu Leu Glu Asp Ser Pro Lys Arg Pro
145                 150                 155                 160

Lys Glu Ala Glu Asn Pro Glu Gly Glu Glu Lys Glu Ala Ala Thr Leu
                165                 170                 175

Glu Val Glu Arg Pro Leu Pro Met Glu Val Glu Lys Asn Ser Thr Pro
            180                 185                 190

Ser Glu Pro Gly Ser Gly Arg Gly Pro Pro Gln Glu Glu Glu Glu Glu
        195                 200                 205

Glu Asp Glu Glu Glu Glu Ala Thr Lys Glu Asp Ala Glu
    210                 215                 220

<210> SEQ ID NO 5
<211> LENGTH: 145
<212> TYPE: PRT
<213> ORGANISM: Homo sapiens

<400> SEQUENCE: 5

Lys Ala Ser Gly Tyr Gln Ser Ser Gln Lys Lys Ser Cys Val Glu Glu
  1               5                  10                  15

Pro Glu Pro Glu Pro Glu Ala Ala Glu Gly Asp Gly Asp Lys Lys Gly
             20                  25                  30

Asn Ala Glu Gly Ser Ser Asp Glu Glu Gly Lys Leu Val Ile Asp Glu
         35                  40                  45

Pro Ala Lys Glu Lys Asn Glu Lys Gly Ala Leu Lys Arg Arg Ala Gly
     50                  55                  60

Asp Leu Leu Glu Asp Ser Pro Lys Arg Pro Lys Glu Ala Glu Asn Pro
 65                  70                  75                  80

Glu Gly Glu Glu Lys Glu Ala Ala Thr Leu Glu Val Glu Arg Pro Leu
                 85                  90                  95

Pro Met Glu Val Glu Lys Asn Ser Thr Pro Ser Glu Pro Gly Ser Gly
            100                 105                 110
```

```
Arg Gly Pro Pro Gln Glu Glu Glu Glu Glu Asp Glu Glu Glu
        115                 120                 125

Ala Thr Lys Glu Asp Ala Glu Ala Pro Gly Ile Arg Asp His Glu Ser
        130                 135                 140

Leu
145

<210> SEQ ID NO 6
<211> LENGTH: 108
<212> TYPE: PRT
<213> ORGANISM: Mus sp.

<400> SEQUENCE: 6

Tyr Lys Cys Gly Asp Leu Val Phe Ala Lys Met Lys Gly Tyr Pro His
 1               5                  10                  15

Trp Pro Ala Arg Ile Asp Glu Met Pro Glu Ala Ala Val Lys Ser Thr
                20                  25                  30

Ala Asn Lys Tyr Gln Val Phe Phe Gly Thr His Glu Thr Ala Phe
            35                  40                  45

Leu Gly Pro Lys Asp Leu Phe Pro Tyr Glu Glu Ser Lys Glu Lys Phe
 50                  55                  60

Gly Lys Pro Asn Lys Arg Lys Gly Phe Ser Glu Gly Leu Trp Glu Ile
 65                  70                  75                  80

Glu Asn Asn Pro Thr Val Lys Ala Ser Gly Tyr Gln Ser Ser Gln Lys
                85                  90                  95

Lys Ser Cys Ala Ala Glu Pro Glu Val Glu Pro Glu
            100                 105

<210> SEQ ID NO 7
<211> LENGTH: 123
<212> TYPE: PRT
<213> ORGANISM: Mus sp.

<400> SEQUENCE: 7

Met Pro His Ala Phe Lys Pro Gly Asp Leu Val Phe Ala Lys Met Lys
 1               5                  10                  15

Gly Tyr Pro His Trp Pro Ala Arg Ile Asp Asp Ile Ala Asp Gly Ala
                20                  25                  30

Val Lys Pro Pro Pro Asn Lys Tyr Pro Ile Phe Phe Gly Thr His
            35                  40                  45

Glu Thr Ala Phe Leu Gly Pro Lys Asp Leu Phe Pro Tyr Asp Lys Cys
 50                  55                  60

Lys Asp Lys Tyr Gly Lys Pro Asn Lys Arg Lys Gly Phe Asn Glu Gly
 65                  70                  75                  80

Leu Trp Glu Ile Gln Asn Asn Pro His Ala Ser Tyr Ser Ala Pro Pro
                85                  90                  95

Pro Val Ser Ser Ser Asp Ser Glu Ala Pro Glu Ala Asp Leu Gly Cys
            100                 105                 110

Gly Ser Asp Val Asp Lys Asp Lys Glu Ser Arg
        115                 120

<210> SEQ ID NO 8
<211> LENGTH: 127
<212> TYPE: PRT
<213> ORGANISM: Homo sapiens

<400> SEQUENCE: 8

Met Thr Arg Asp Phe Lys Pro Gly Asp Leu Ile Phe Ala Lys Met Lys
```

-continued

```
                1               5                   10                  15
Gly Tyr Pro His Trp Pro Ala Arg Val Asp Glu Val Pro Asp Gly Ala
            20                  25                  30

Val Lys Pro Pro Thr Asn Lys Leu Pro Ile Phe Phe Phe Gly Thr His
        35                  40                  45

Glu Thr Ala Phe Leu Gly Pro Lys Asp Ile Phe Pro Tyr Ser Glu Asn
    50                  55                  60

Lys Glu Lys Tyr Gly Lys Pro Asn Lys Arg Lys Gly Phe Asn Glu Gly
65                  70                  75                  80

Leu Trp Glu Ile Asp Asn Asn Pro Lys Val Lys Phe Ser Ser Gln Gln
                85                  90                  95

Ala Ala Thr Lys Gln Ser Asn Ala Ser Ser Asp Val Glu Val Glu Glu
            100                 105                 110

Lys Glu Thr Ser Val Ser Lys Glu Asp Thr Asp His Glu Glu Lys
        115                 120                 125
```

<210> SEQ ID NO 9
<211> LENGTH: 127
<212> TYPE: PRT
<213> ORGANISM: Homo sapiens

<400> SEQUENCE: 9

```
Met Thr Arg Asp Phe Lys Pro Gly Asp Leu Ile Phe Ala Lys Met Lys
1               5                   10                  15

Gly Tyr Pro His Trp Pro Ala Arg Val Asp Glu Val Pro Asp Gly Ala
            20                  25                  30

Val Lys Pro Pro Thr Asn Lys Leu Pro Ile Phe Phe Phe Gly Thr His
        35                  40                  45

Glu Thr Ala Phe Leu Gly Pro Lys Asp Ile Phe Pro Tyr Ser Glu Asn
    50                  55                  60

Lys Glu Lys Tyr Gly Lys Pro Asn Lys Arg Lys Gly Phe Asn Glu Gly
65                  70                  75                  80

Leu Trp Glu Ile Asp Asn Asn Pro Lys Val Lys Phe Ser Ser Gln Gln
                85                  90                  95

Ala Ala Thr Lys Gln Ser Asn Ala Ser Ser Asp Val Glu Val Glu Glu
            100                 105                 110

Lys Glu Thr Ser Val Ser Lys Glu Asp Thr Asp His Glu Glu Lys
        115                 120                 125
```

<210> SEQ ID NO 10
<211> LENGTH: 109
<212> TYPE: PRT
<213> ORGANISM: Mus sp.

<400> SEQUENCE: 10

```
Tyr Lys Thr Gly Asp Leu Val Phe Ala Lys Leu Lys Gly Tyr Ala His
1               5                   10                  15

Trp Pro Ala Arg Ile Glu His Val Ala Glu Ala Asn Arg Tyr Gln Val
            20                  25                  30

Phe Phe Phe Gly Thr His Glu Thr Ala Leu Leu Gly Pro Arg His Leu
        35                  40                  45

Phe Pro Tyr Glu Glu Ser Lys Glu Lys Phe Gly Lys Pro Asn Lys Arg
    50                  55                  60

Arg Gly Phe Ser Glu Gly Leu Trp Glu Ile Glu His Asp Pro Met Val
65                  70                  75                  80

Glu Ala Ser Ser Ser Leu Cys Ser Glu Glu Asp Gln Ser Tyr Thr Glu
```

```
              85                  90                  95
Asp Pro Gly Leu Ala Glu Glu Pro Glu Leu Gly Gln Glu
            100                 105
```

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
ggatccacca tgtcggccta cggcatgccc atgtac                    36

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
ctcgagcagg ctgtcgcgat ctccgccgcc                           30

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 13
gacaagccga cccacgctgg                                      20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 14
ccagcgtggg tcggcttgtc                                      20

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 15
ctcgtcctcg agggtaagcc tatccctaac                           30

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence:
      oligonucleotide

```
<400> SEQUENCE: 16
ctcgtcgggc ccctgatcag cgggtttaaa c                              31

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17
accaggtgtt tttcttcggg a                                         21

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
ccacgagacg gccttcctga gtcc                                      24

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 19
ttgtacggga acaggcgttt                                           20

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 20
accaggtgtt tttcttcggg a                                         21

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 21
ccacgagacg gccttcctga gtcc                                      24

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 22
```

```
ttgtacggga acaggcgttt                                          20
```

HEPATOMA-DERIVED GROWTH FACTOR-LIKE PROTEINS, POLYNUCLEOTIDES ENCODING THEM AND METHODS OF USE

RELATED APPLICATIONS

This application claims priority to provisional application U.S. Ser. No. 60/156,975, filed Oct. 1, 1999, the content of which is incorporated herein by reference in its entirety.

FIELD OF THE INVENTION

The invention generally relates to novel nucleic acids and polypeptides and more particularly to novel nucleic acids encoding polypeptides related to growth factors.

BACKGROUND OF THE INVENTION

Hepatoma-derived growth factor (HDGF) and HDGF-related proteins (HRP) belong to a gene family with a well-conserved amino acid sequence at the N-terminus. Hepatoma-derived growth factor HDGF was the first member identified in this new family of secreted heparin-binding growth factors that are highly expressed in the fetal aorta. Like other heparin binding proteins, HDGF is an acidic polypeptide with mitogenic activity for fibroblasts The biologic role of HDGF in vascular growth is unknown. However, HDGF colocalizes with the proliferating cell nuclear antigen (PCNA) in smooth muscles cells in human atherosclerotic carotid arteries, suggesting that HDGF helps regulate smooth muscle growth during development and in response to vascular injury.

SUMMARY OF THE INVENTION

The present invention is based, in part, upon the discovery of a nucleic acid encoding a novel polypeptide having homology to hepatoma-derived growth factor (HDGF) protein. The novel hepatoma-derived growth factor X (HDGFX) polynucleotide sequences and the HDGFX polypeptides encoded by these nucleic acid sequences, and fragments, homologs, analogs, and derivatives thereof, are claimed in the invention.

In one aspect, the invention provides an isolated HDGFX nucleic acid (SEQ ID NO:1, as shown in Table 1), that encodes a HDGFX polypeptide, or a fragment, homolog, analog or derivative thereof. The nucleic acid can include, e.g., nucleic acid sequence encoding a polypeptide at least 85% identical to a polypeptide comprising the amino acid sequence of Table 1 (SEQ ID NO:2). The nucleic acid can be, e.g., a genomic DNA fragment, or it can be a cDNA molecule. In another aspect, the invention provides a complement to the HDGFX nucleic acid shown in Table 1, or a fragment, homolog, analog or derivative thereof.

Also included in the invention is a vector containing one or more of the nucleic acids described herein, and a cell containing the vectors or nucleic acids described herein.

The present invention is also directed to host cells transformed with a recombinant expression vector comprising any of the nucleic acid molecules described above.

In one aspect, the invention includes a pharmaceutical composition that includes a HDGFX nucleic acid and a pharmaceutically acceptable carrier or diluent. In a further aspect, the invention includes a substantially purified HDGFX polypeptide, e.g., any of the HDGFX polypeptides encoded by a HDGFX nucleic acid, and fragments, homologs, analogs, and derivatives thereof. The invention also includes a pharmaceutical composition that includes a HDGFX polypeptide and a pharmaceutically acceptable carrier or diluent.

In a further aspect, the invention provides an antibody that binds specifically to a HDGFX polypeptide. The antibody can be, e.g., a monoclonal or polyclonal antibody, and fragments, homologs, analogs, and derivatives thereof. The invention also includes a pharmaceutical composition including HDGFX antibody and a pharmaceutically acceptable carrier or diluent. The present invention is also directed to isolated antibodies that bind to an epitope on a polypeptide encoded by any of the nucleic acid molecules described above.

The present invention is further directed to kits comprising antibodies that bind to a polypeptide encoded by any of the nucleic acid molecules described above and a negative control antibody.

The invention further provides a method for producing a HDGFX polypeptide. The method includes providing a cell containing a HDGFX nucleic acid, e.g., a vector that includes a HDGFX nucleic acid, and culturing the cell under conditions sufficient to express the HDGFX polypeptide encoded by the nucleic acid. The expressed HDGFX polypeptide is then recovered from the cell. Preferably, the cell produces little or no endogenous HDGFX polypeptide. The cell can be, e.g., a prokaryotic cell or eukaryotic cell.

The present invention provides a method of inducing an immune response in a mammal against a polypeptide encoded by any of the nucleic acid molecules disclosed above. In one embodiment, the method includes administering to the mammal an amount of the polypeptide sufficient to induce the immune response. In another embodiment, the method includes administering to the mammal a nucleic acid encoding a HDGFX polypeptide in an amount sufficient to produce enough HDGFX polypeptide to induce the immune response.

The present invention is also directed to methods of identifying a compound that binds to HDGFX polypeptide by contacting the HDGFX polypeptide with a compound and determining whether the compound binds to the HDGFX polypeptide.

The invention further provides methods of identifying a compound that modulates the activity of a HDGFX polypeptide by contacting HDGFX polypeptide with a compound and determining whether the HDGFX polypeptide activity is modified.

The present invention is also directed to compounds that modulate HDGFX polypeptide activity identified by contacting a HDGFX polypeptide with the compound and determining whether the compound modifies activity of the HDGFX polypeptide, binds to the HDGFX polypeptide, or binds to a nucleic acid molecule encoding a HDGFX polypeptide.

In a further aspect, the invention includes a method of diagnosing a tissue proliferation-associated disorder, such as tumors, restenosis, psoriasis, diabetic and post-surgery complications, and rheumatoid arthritis, in a subject. The method includes providing a nucleic acid sample, e.g., RNA or DNA, or both, from the subject and measuring the amount of the HDGFX nucleic acid in the subject nucleic acid sample. The amount of HDGFX nucleic acid sample in the subject nucleic acid is then compared to the amount of HDGFX nucleic acid in a control sample. An alteration in the amount of HDGFX nucleic acid in the sample relative to the amount of HDGFX in the control sample indicates the subject has a tissue proliferation-associated disorder.

In a still further aspect, the invention provides method of treating or preventing or delaying a tissue proliferation-associated disorder. The method includes administering to a subject in which such treatment or prevention or delay is desired a HDGFX nucleic acid, a HDGFX polypeptide, or a HDGFX antibody in an amount sufficient to treat, prevent, or delay a tissue proliferation-associated disorder in the subject.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

Figure 1:
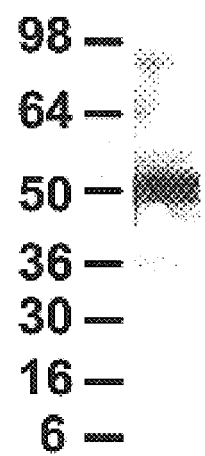
FIG. 1. Western blot of the HDGFX (also referred to as AL033539) polypeptide secreted by 293 cells.

Included in the invention is HDGFX (also referred to as AL033539_A), a novel hepatoma-derived growth factor ("HDGF") related polypeptide, and nucleic acids encoding the polypeptide. Antibodies that bind specifically to HDGFX polypeptides, or fragments thereof, are included in the invention. The invention further includes fragments, homologs, analogs, and derivatives of HDGFX nucleic acids, polypeptides, and antibodies.

A DNA sequence of a human HDGFX gene (880 nucleotides; SEQ ID NO:1), and its encoded amino acid sequence (SEQ ID NO:2), are shown in Table 1. The translated protein is encoded from nucleotide 79 to 831. The HDGFX protein product (SEQ ID NO:2) is 251 amino acids in length. The predicted molecular weight of the HDGFX polypeptide is 27,233.3 daltons. The protein of SEQ ID NO:2 is predicted by the PSORT software program to localize in the nucleus with a certainty of 0.8800.

The protein of the invention encoded by clone HDGFX_A includes the full protein disclosed as being encoded by the ORF described herein, as well as any mature protein arising therefrom as a result of posttranslational modifications. Thus, the proteins of the invention encompass both a precursor and any active forms of the HDGFX_A protein.

The software programs PSORT and SignalP predicts that HDGFX contains no signal peptide.

TABLE 1

Hepatoma-Derived Growth Factor
Homolog Polynucleotide (SEQ ID NO:1)
and Amino Acid (SEQ ID NO:2) Sequences

```
  1 GCAGCCGCCCTTACTGCGCGCGCGCAGACTTCGGCGTCTACTTCC

46 GGTGTGGCCCAGGCGGGGTCCGCAGAACCAGCTATGTCGGCCTAC
                                        MetSerAlaTyr

91 GGCATGCCCATGTACAAGAGCGGGGACCTGGTGTTTGCCAAGTTA
    GlyMetProMetTyrLysSerGlyAspLeuValPheAlaLysLeu

136 AAGGGCTATGCCCACTGGCCGGCGAGGATAGAGCACATGACCCAG
    LysGlyTyrAlaHisTrpProAlaArgIleGluHisMetThrGln

181 CCCAACCGCTACCAGGTGTTTTTCTTCGGGACCCACGAGACGGCC
    ProAsnArgTyrGlnValPhePhePheGlyThrHisGluThrAla

226 TTCCTGAGTCCCAAACGCCTGTTCCCGTACAAGGAGTGCAAGGAG
    PheLeuSerProLysArgLeuPheProTyrLysGluCysLysGlu

271 AAGTTCGGCAAGCCCAACAAGAGGCGCGGCTTCAGCGCGGGCTG
    LysPheGlyLysProAsnLysArgArgGlyPheSerAlaGlyLeu

316 TGGGAAATCGAGAACAACCCCACGGTCCAGGCCTCCGACTGCCCA
    TrpGluIleGluAsnAsnProThrValGlnAlaSerAspCysPro

361 TTAGCCTCAGAGAAGGGCAGCGGAGACGGGCCTTGGCCGGAGCCC
    LeuAlaSerGluLysGlySerGlyAspGlyProTrpProGluPro

406 CAGGCCGCAGAGGGCGACGAGGACAAGCCGACCCACGCTGGTGGC
    GluAlaAlaGluGlyAspGluAspLysProThrHisAlaGlyGly

451 GGCGGCGACGAATTGGGGAAGCCGGACGACGACAAGCCCACTGAG
    GlyGlyAspGluLeuGlyLysProAspAspAspLysProThrGlu

496 GAGGAGAAGGGGCCGCTGAAGAGGAGCGCGGGGGACCCGCCGGAG
    GluGluLysGlyProLeuLysArgSerAlaGlyAspProProGlu

541 GACGCCCCAAACGACCCAAGGAGGCAGCCCCCGACCAAGAGGAG
    AspAlaProLysArgProLysGluAlaAlaProAspGlnGluGlu

586 GAGGCGGAGGCGGAGAGGGCGGCGGAAGCGGAGAGGGCGGCGGCG
    GluAlaGluAlaGluArgAlaAlaGluAlaGluArgAlaAlaAla

631 GCGGCGGCGGCGACGGCCGTCGACGAGGAGAGTCCGTTCCTCGTG
    AlaAlaAlaAlaThrAlaValAspGluGluSerProPheLeuVal

676 GCGGTGGAGAACGGCAGCGCCCCTAGCGAGCCGGGCCTGGTCTGC
    AlaValGluAsnGlySerAlaProSerGluProGlyLeuValCys

721 GAGCCGCCTCAGCCAGAGGAGGAGGAGCTCCGGGAGGAAGAAGTC
    GluProProGlnProGluGluGluGluLeuArgGluGluGluVal

766 GCGGACGAGGAGGCCTCCCAGGACTGGCATGCCGAGGCACCGGGC
    AlaAspGluGluAlaSerGlnGluTrpHisAlaGluAlaProGly

811 GGCGGAGATCGCGACAGCCTGTAGTTACCAGCGTTTCCAGAAGAG
    GlyGlyAspArgAspSerLeu

856 CCCCTGCCCCGTTCCTGCTGCGGCC
```

A search of the sequence databases using BLASTP and BLASTX programs reveals that the HDGFX_A protein product (SEQ ID NO:2) has 143 of 234 residues (61%) identical to, and 155 of 243 residues (66%) positive with, the 235 residue bovine hepatoma derived growth factor related protein 3 (HRP-3) (TREMBLNEW-ACC:CAB40348). Alignment results are shown in Table 2

TABLE 2

BLAST Results showing HDGFX vs. HRP-3
(Query = HDGFX; Sbjct = HRP-3 (SEQ ID NO:3))

```
ptnr:TREMBLNEW-ACC:CAB40348 HEPATOMA DERIVED GROWTH FACTOR RELATED PROTEIN 3
(HRP-3) - Bos
taurus(Bovine), 235 aa.
Plus Strand HSPs:
Score = 640 (225.3 bits), Expect = 6.2e-62, P = 6.2e-62
Identities = 143/234 (61%), Positives = 155/234 (66%), Frame = +1
Query:  79 MSAYGMPMYKSGDLVFAKLKGYAHWPARIEHMTQPNRYQVFFFGTHETAFLSPKRLFPYK 258
              ||  +     ||  |||||||||||||||||   +  |||||||||||||||  |+  ||||+
Sbjct:   1 MSRFYRRKYKCGDLVFAKLKGYAHWPARIEQTAEANRYQVFFFGTHETAFLGPRHLFPYE 60

Query: 259 ECKEKFGKPNKRRGFSAGLWEIENNPTVQASDCPLASEKGSGDGPWPEPEAAEGDEDKPT 438
           | ||||||||||||||||  |||||||||||||||||   |  ||   +  |     |||   ||  ||   +
Sbjct:  61 ESKEKFGKPNKRRGFSEGLWEIENNPTVQASDYQCALEKSCPEEP--EPEVAEGGEDPKS 118

Query: 439 HAGGGGDE-LGKPDDDKPTEEE--KGPLKRSAGDPPEDAPKRPKEAAPDQEEEAEAERAA 609
           |   ||  |+  ||    | |  |||    |   ||+|  |||||  |||||   ||  |+
Sbjct: 119 HTNGGDDDQGKLGVDLPAEEENKKETLKRTAEDPPEDIPKRPKEADP---EEGE----- 170

Query: 610 EAERAAAAAAATAVDEESPFLVAVENGSAPSEPGLVCEPPQPEEEELREEEVADEEA 780
              ||  |||   |   ++   |  ||| |  |    |  |+|    |||  |+  ||
Sbjct: 171 --ERKEAAAVAEEAEDARPLLVEVENDPAASVLGLAWGLPVMEQEP--EEESAEREA 223
```

HDGFX protein product (SEQ ID NO:2) was also found to have 135 of 228 residues (59%) identical to, and 156 of 228 residues (68%) positive with the 240 residue human hepatoma-derived growth factor (HDGF) protein (SWISSPROT-ACC:P51858). Alignment results are shown in TABLE 3, sections A and B.

TABLE 3

BLAST Results showing HDGFX vs. HDG

A. Query = HDGFX; Sbjct = HDGF (SEQ ID NO:4)

```
ptnr:SWISSPROT-ACC:P51858 HEPATOMA-DERIVED GROWTH FACTOR (HDGF) - Homo
sapiens, 240 aa.
Length = 240
Score = 608 (214.0 bits), Expect = 2.6e-59, P = 2.6e-59
Identities = 135/228 (59%), Positives = 156/228 (68%)
Query:   9 YKSGDLVFAKLKGYAHWPARIEHMTQP------NRYQVFFFGTHETAFLSPKRLFPYKEC 62
           ||  ||||||+|||  ||||||+  +           |+|||||||||||||  ||  ||||+
Sbjct:  10 YKCGDLVFAKMKGYPHWPARIDEMPEAAVKSTANKYQVFFFGTHETAFLGPKDLFPYEES 69

Query:  63 KEKFGKPNKRRGFSAGLWEIENNPTVQASDCPLASEKGSGDGPWPEPEAAEGDEDKPTHA 122
           |||||||||+|||  ||||||||||||+||    ++|     +  |  |||||||||  ||   +|
Sbjct:  70 KEKFGKPNKRKGFSEGLWEIENNPTVKASGYQSSQKKSCVEEPEPEPEAAEGDGDKKGNA 129

Query: 123 GGGGDELGKPDDDKPTEE--EKGPLKRSAGDPPEDAPKRPKEAAPDQEEEAEAERAAEAE 180
           |      ||  ||   |+  +|   |||  ||||   ||+||||||   +  ||  ||  +|
Sbjct: 130 EGSSDEEGKLVIDEPAKEKNEKGALKRRAGDLLEDSPKRPKEAENPEGEEKEA------- 182

Query: 181 RAAAAAAATAVDEESPFLVAVENGSAPSEPGLVCEPPQPEEEELREEEVADEEASQ 236
                     ||  ++  |  |  +  ||  |||||    |||   +|  ++
Sbjct: 183 -------AT-LEVERPLPMEVEKNSTPSEPGSGRGPPQEEEEEEDEEEEATKEDAE 230
```

B. Query = HDGFX; Sbjct = HDGF (SEQ ID NO:5)

```
ptnr:SWISSPROT-ACC:P515S HEPATOMA-DERIVED GROWTH FACTOR (HDGF) - Homo
sapiens, 240 aa.
Score = 161 (56.7 bits), Expect = 1.2e-10, P = 1.2e-10
Identities = 54/153 (35%), Positives = 73/153 (47%)
Query:  99 KGSGDGPWPEPEAAEGDEDKPTHAGGGGDELDKPDDDKPTEEEKGPLKRSAGDPPEDAPK 158
           |  ||        +        |   |+|  |  ||+ |  +    ||   +    | +  |
Sbjct:  96 KASGYQSSQKKSCVEEPEPEPEAAEGDGDKKGNAEGSSK--EEGKLVIDEPAKEKNEKGAL 154

Query: 159 RPKEAAPDQEEEAEAERAAEAERAAAAAAATAVDEESPFLVAVENGSAPSEPGLVCEPPQ 218
            + + |    |+  +  +||    |||  ++  |  |  +||   |||||   |||
Sbjct: 155 K-RRAGDLLEDSPKRPKEAENPEGEEKEAAT-LEVERPLPMEVEKNSTPSEPGSGRGPPQ 212

Query: 219 PEEEELREEEVADEEASQEWHAEAPGGGDRDSL 251
           ||||  |+|  +|||++|   |||||    +||
Sbjct: 213 EEEE--EDE--EEEATKE-DAEAPGIRDHESL 240
```

A search of the PRODOM database (E-value cutoff of 0.000001) revealed that the HDGFX polypeptide sequence is homologous to a family of growth factors (TABLE 4, black shading indicates identity and gray shading indicates conservative substitution). The length and complexity of the homology between the family members in Table 4 have a probability of less than $7e^{-27}$ that the conservation between these sequences occurred by chance alone. See, Altschul et al., 1997 Nucl. Acids Res. 25: 3389–3402. Proteins found to be homologous include amino acids 10–117 of mouse HDGF (SEQ ID NO:6) (SWISS-PROT: P51859), amino acids 1–123 of another mouse HDGFRP2 (SEQ ID NO:7) (SWISS-PROT:035540), amino acids 1–127 of human LEDGF (SEQ ID NO:8) (SWISS-PROT: 075475), amino acids 1–127 of another human LEDGF (SEQ ID NO:9) (SWISS:PROT: 075475), and amino acids 9–117 of mouse HDGFRP1 (SEQ ID NO:10) (SWISS-PROT:035539).

novel members of the protein families according to the presence of domains and sequence relatedness to previously described proteins. For example, the HDGFX nucleic acids and their encoded polypeptides include structural motifs that are characteristic of proteins belonging to the hepatoma derived growth factor. Proteins belonging to this family of proteins have been implicated in modulating and inhibiting angiogenesis. Angiogenesis is an important normal physiologic process in embryogenesis, wound repair and the female reproductive cycle. However, as a pathological process, it plays a central role in chronic inflammation, fibroproliferative disorders and tumorigenesis. Thus, HDGFX nucleic acids and polypeptides, antibodies and related compounds according to the invention will be useful in therapeutic applications implicated in various cancers, coronary artery disease, arthritis, and diabetic retinopathy.

TABLE 4

```
                            10        20        30        40        50        60
                      ....|....|....|....|....|....|....|....|....|....|....|....|
HDGFX        (9-113)  ----KSGDLVFAKKGYAHWPARIHTP------NYQVPFFGTHETAPLSPKRLFP  50
HDGF_MOUSE   (10-117) ----KCGDLVFAKMKGYPHWPARIDEPAAVKSTANKYQVFFFGTHETAFLGPKDLFP  56
035540_MOUSE (1-123)  MPHAFKPGDLVFAKMKGYPHWPARIDAGAVKPPNKYPFFFGTHETAFLGPKDLFP   60
075475_HUMAN (1-127)  MTRDFKPGDLFAKMKGYPHWPARVDEPGAVKPPTNKLPFFFGTHETAFLGPKDFP   60
095368_HUMAN (1-127)  MTRDFKPGDLFAKMKGYPHWPARVDEPGAVKPPTNKLPFFFGTHETAFLGPKDFP   60
035539_MOUSE (9-117)  ----KTGDLVFAKKGYAHWPARIHAA------NYQVFFFGTHETALLGPHLFP    50

70        80        90       100       110       120
                      ....|....|....|....|....|....|....|....|....|....|....|....|
HDGFX        (9-113)  YKECKEKGKPNKRGFAGLWEINNETVASDCPLGGDGPWPEPAAE-----         105
HDGF_MOUSE   (10-117) YEEKEKGKPNKRKGFEGLWEINNETVASGYQSQSCANEPEVEPE--------     108
035540_MOUSE (1-123)  YDCKKGKPNKRKGFNEGLWEINNEHASYSPPPVSDSEAPEALGCGS           115
075475_HUMAN (1-127)  YSDKEKGKPNKRKGFNEGLWEINNEKVFSQQASAASDVEVEEKTSVSK          120
095368_HUMAN (1-127)  YSDKEKGKPNKRKGFNEGLWEINNEKVFSQQASAASDVEVEEKTSVSK          120
035539_MOUSE (9-117)  YEDKEKGKPNKRGFEGLWEIHDEMVASSLCEDQYEDPGLAE-PELGQ           109

....|....
HDGFX        (9-113)  --------   105
HDGF_MOUSE   (10-117) --------   108
035540_MOUSE (1-123)  VDKDKESR   127
075475_HUMAN (1-127)  -DTDHEEK   127
095368_HUMAN (1-127)  -DTDHEEK   127
035539_MOUSE (9-117)  --------   109
```

HDGFX nucleic acids, and their encoded polypeptides, according to the invention are useful in a variety of applications and contexts. For example, HDGFX nucleic acids and polypeptides can be used to identify proteins that are members of the hepatoma derived growth factor family. The HDGFX nucleic acids and polypeptides can also be used to screen for molecules which inhibit or enhance HDGF activity or function. Specifically, the nucleic acids and polypeptides according to the invention may be used as targets for the identification of small molecules that modulate or inhibit, e.g., angiogenesis neuronal development or spermatogenesis. These molecules can be used to treat, e.g., cancer, neurological disorders or infertility in mammals, e.g. humans.

In addition, various HDGFX nucleic acids and polypeptides according to the invention are useful, inter alia, as Immunofluorescence data indicate that HDGF is localized in the cytoplasm of hepatoma cells and is expressed ubiquitously in normal tissues and tumor cell lines. See, e.g., Nakamura et al., 1994 J. Biol. Chem. 269: 25143–25149. Therefore, in an alternative embodiment, HDGFX, including the human hepatoma-derived growth factor homolog according to the invention, may be a cytosolic protein with a synthetic signal peptide. Nakamura et al. suggests that HDGF is a likely novel heparin-binding protein with mitogenic activity for fibroblasts performed outside the cells, despite the presence of a putative nuclear localization signal. Therefore, in another embodiment, HDGFX may serve as novel growth-modulating factor to which various cells and tissues in the human body respond. (see, EXAMPLE 8).

In addition, HDGFX nucleic acids, polypeptides, antibodies and related compounds of the invention may be used to modulate spermatogenesis, stimulate smooth muscle growth and modulate neuronal development.

In-vivo studies with purified HDGFX proteins, as shown in EXAMPLE 7 below, demonstrate an increase of splenic extramedullary hematopoiesis and lymhoid hyperplasia. This indicates potential therapeutic and diagnostic applications of HDGFX nucleic acids and polypeptides antibodies and related compounds of the invention in treating blood related disorders by, e.g,modulating hematopoiesis and immunological related disorders by, e.g., stimulating the immune system.

Additional utilities for HDGFX nucleic acids and polypeptides according to the invention are disclosed herein.

HDGFX Nucleic Acids

The novel nucleic acids of the invention include those that encode a HDGFX, HDGFX-like polypeptide or biologically active portions thereof. Among these nucleic acids is the nucleic acid whose sequence is provided in SEQ ID NO:1, or a fragment, derivative, or homolog thereof. Additionally, the invention includes mutant or variant nucleic acids of SEQ ID NO:1, or a fragment thereof, any of whose bases may be changed from the corresponding base shown in SEQ ID NO:1 while still encoding a protein that maintains its HDGFX-like activities and physiological functions. The invention further includes the complement of the nucleic acid sequence of SEQ ID NOs:1, including fragments, derivatives, analogs and homolog thereof. Examples of the complementary strand of portions of HDGFX are shown as oligonucleotide primers in the EXAMPLES section. The invention additionally includes nucleic acids or nucleic acid fragments, or complements thereto, whose structures include chemical modifications.

Additional nucleic acids include nucleic acids encoding HDGFX polypeptides that include the amino acid sequence of of SEQ ID NO:2. In some embodiments, a nucleic acid encoding a polypeptide having the amino acid sequence of of SEQ ID NO:2 includes the nucleic acid sequence of SEQ ID NO:1, or a fragment thereof.

Additionally, a HDGFX nucleic acid of the invention includes mutant or variant nucleic acids of SEQ ID NO:1, or a fragment thereof, any of whose bases may be changed from the disclosed sequence while still encoding a protein that maintains its HDGFX-like activities and physiological functions. The invention further includes the complement of the nucleic acid sequence of SEQ ID NO:1, including fragments, derivatives, analogs and homolog thereof. The invention additionally includes nucleic acids or nucleic acid fragments, or complements thereto, whose structures include chemical modifications.

A HDGFX nucleic acid of the invention can encode a mature form of a HDGFX polypeptide. As used herein, a "mature" form of a polypeptide or protein is the product of a naturally occurring polypeptide or precursor form or proprotein. The naturally occurring polypeptide, precursor or proprotein includes, by way of nonlimiting example, the full length gene product, encoded by the corresponding gene. Alternatively, it may be defined as the polypeptide, precursor or proprotein encoded by an open reading frame described herein. The product "mature" form arises, again by way of nonlimiting example, as a result of one or more naturally occurring processing steps as they may take place within the cell, or host cell, in which the gene product arises. Examples of such processing steps leading to a "mature" form of a polypeptide or protein include the cleavage of the N-terminal methionine residue encoded by the initiation codon of an open reading frame, or the proteolytic cleavage of a signal peptide or leader sequence. Thus a mature form arising from a precursor polypeptide or protein that has residues 1 to N, where residue 1 is the N-terminal methionine, would have residues 2 through N remaining after removal of the N-terminal methionine. Alternatively, a mature form arising from a precursor polypeptide or protein having residues 1 to N, in which an N-terminal signal sequence from residue 1 to residue M is cleaved, would have the residues from residue M+1 to residue N remaining. Additionally, a "mature" protein or fragment may arise from a cleavage event other than removal of an initiating methionine or removal of a signal peptide. Further as used herein, a "mature" form of a polypeptide or protein may arise from a step of post-translational modification other than a proteolytic cleavage event. Such additional processes include, by way of non-limiting example, glycosylation, myristylation or phosphorylation. In general, a mature polypeptide or protein may result from the operation of only one of these processes, or a combination of any of them.

Also included are nucleic acid fragments.sufficient for use as hybridization probes to identify nucleic acids encoding HDGFX polypeptides (e.g., a HDGFX mRNA encoding SEQ ID NO:2) and fragments for use as polymerase chain reaction (PCR) primers for the amplification or mutation of HDGFX nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but preferably is double-stranded DNA.

"Probes" refer to nucleic acid sequences of variable length, preferably between at least about 10 nucleotides (nt), 20 nt, 30 nt, 50 nt, 100 nt, 500 nt, 1000 nt, or as many as about, e.g., 6,000 nt, depending on use. Probes are used in the detection of identical, similar, or complementary nucleic acid sequences. Longer length probes are usually obtained from a natural or recombinant source (although they may be prepared by chemical synthesis as well), are highly specific and much slower to hybridize than oligomers. Probes may be single- or double-stranded and designed to have specificity in PCR, membrane-based hybridization technologies, or ELISA-like technologies.

An "isolated" nucleic acid molecule is one that is separated from other nucleic acid molecules that are present in the natural source of the nucleic acid. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated HDGFX nucleic acid molecule can contain less than about 50 kb, 25 kb, 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized.

A nucleic acid molecule of the present invention, e.g., a nucleic acid molecule having the nucleotide sequence of SEQ ID NO:1, or a complement of this nucleotide sequence, can be isolated using standard molecular biology techniques and the sequence information provided herein. Using all or a portion of the nucleic acid sequence of SEQ ID NO:1 as a hybridization probe, HDGFX nucleic acid sequences can be isolated using standard hybridization and cloning techniques (e.g., as described in Sambrook et al., eds., MOLECULAR CLONING: A LABORATORY MANUAL $2^{nd}$ Ed., Cold Spring Harbor Laboratory Press, Cold Spring Harbor, N.Y., 1989; and Ausubel, et al., eds., CURRENT PROTOCOLS IN MOLECULAR BIOLOGY, John Wiley & Sons, New York, N.Y., 1993.)

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to HDGFX nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nt in length, preferably about 15 nt to 30 nt in length. In one embodiment, an oligonucleotide comprising a nucleic acid molecule less than 100 nt in length would further comprise at lease 6 contiguous nucleotides of SEQ ID NO:1, or a complement thereof. Oligonucleotides may be chemically synthesized and may be used as probes.

In another embodiment, an isolated nucleic acid molecule of the invention comprises a nucleic acid molecule that is a complement of the nucleotide sequence shown in any of SEQ ID NO:1. In another embodiment, an isolated nucleic acid molecule of the invention comprises a nucleic acid molecule that is a complement of the nucleotide sequence shown in any of SEQ ID NO:1, or a portion of this nucleotide sequence. A nucleic acid molecule that is complementary to the nucleotide sequence shown in SEQ ID NO:1 is one that is sufficiently complementary to the nucleotide sequence shown in of SEQ ID NO:1 that it can hydrogen bond with little or no mismatches to the nucleotide sequence shown in of SEQ ID NO:1, thereby forming a stable duplex.

As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, van der Waals, hydrophobic interactions, etc. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Moreover, the nucleic acid molecule of the invention can comprise only a portion of the nucleic acid sequence of SEQ ID NO:1, e.g., a fragment that can be used as a probe or primer, or a fragment encoding a biologically active portion of HDGFX. "Fragments" provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. "Derivatives" are nucleic acid sequences or amino acid sequences formed from the native compounds either directly or by modification or partial substitution. "Analogs" are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 70%, 80%, 85%, 90%, 95%, 98%, or even 99% identity (with a preferred identity of 80–99%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel, et al., CURRENT PROTOCOLS IN MOLECULAR BIOLOGY, John Wiley & Sons, New York, N.Y., 1993, and below. An exemplary program is the Gap program (Wisconsin Sequence Analysis Package, Version 8 for UNIX, Genetics Computer Group, University Research Park, Madison, Wis.) using the default settings, which uses the algorithm of Smith and Waterman (Adv. Appl. Math., 1981, 2: 482–489, which is incorporated herein by reference in its entirety).

A "homologous nucleic acid sequence" or "homologous amino acid sequence," or variations thereof, refer to sequences characterized by a homology at the nucleotide level or amino acid level as discussed above. Homologous nucleotide sequences encode those sequences coding for isoforms of a HDGFX polypeptide. Isoforms can be expressed in different tissues of the same organism as a result of, for example, alternative splicing of RNA. Alternatively, isoforms can be encoded by different genes. In the present invention, homologous nucleotide sequences include nucleotide sequences encoding for a HDGFX polypeptide of species other than humans, including, but not limited to, mammals, and thus can include, e.g., mouse, rat, rabbit, dog, cat cow, horse, and other organisms. Homologous nucleotide sequences also include, but are not limited to, naturally occurring allelic variations and mutations of the nucleotide sequences set forth herein. A homologous nucleotide sequence does not, however, include the nucleotide sequence encoding human HDGFX protein. Homologous nucleic acid sequences include those nucleic acid sequences that encode conservative amino acid substitutions (see below) in any of SEQ ID NO:2 as well as a polypeptide having HDGFX activity. Biological activities of the HDGFX proteins are described herein.

As used herein, "identical" residues correspond to those residues in a comparison between two sequences where the equivalent nucleotide base or amino acid residue in an alignment of two sequences is the same residue. Residues are alternatively described as "similar" or "positive" when the comparisons between two sequences in an alignment show that residues in an equivalent position in a comparison are either the same amino acid or a conserved amino acid as defined below.

The nucleotide sequence determined from the cloning of the human HDGFX gene allows for the generation of probes and primers designed for use in identifying the cell types disclosed and/or cloning HDGFX protein homologues in other cell types, e.g., from other tissues, as well as HDGFX homologues from other mammals. The probe/primer typically comprises a substantially purified oligonucleotide. The oligonucleotide typically comprises a region of nucleotide sequence that hybridizes under stringent conditions to at least about 12, 25, 50, 100, 150, 200, 250, 300, 350 or 400 or more consecutive sense strand nucleotide sequence of SEQ ID NO:1; or an anti-sense strand nucleotide sequence of SEQ ID NO:1; or of a naturally occurring mutant of SEQ ID NO:1.

Probes based on a human HDGFX nucleotide sequence can be used to detect transcripts or genomic sequences encoding the same or homologous proteins. In various embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a HDGFX protein, such as by measuring a level of a HDGFX protein-encoding nucleic acid in a sample of cells from a subject e.g., detecting mRNA levels or determining whether a genomic HDGFX gene has been mutated or deleted.

"A polypeptide having a biologically active portion of a HDGFX" refers to polypeptides exhibiting activity similar, but not necessarily identical to, an activity of a polypeptide of the present invention, including mature forms, as measured in a particular biological assay, with or without dose dependency. A nucleic acid fragment encoding a "biologically active portion of a HDGFX polypeptide" can be prepared by isolating a portion of SEQ ID NO:1 that encodes a polypeptide having a HDGFX polypeptide biological activity such as those disclosed herein, expressing the encoded portion of HDGFX protein (e.g., by recombinant expression in vitro) and assessing the activity of the encoded portion of the HDGFX polypeptide.

HDGFX Variants

The invention further encompasses nucleic acid molecules that differ from the disclosed HDGFX nucleotide sequences due to degeneracy of the genetic code. These nucleic acids thus encode the same HDGFX protein as that encoded by the nucleotide sequence shown in SEQ ID NO:1. In another embodiment, an isolated nucleic acid molecule of the invention has a nucleotide sequence encoding a protein having an amino acid sequence shown in any of SEQ ID NO:2.

In addition to the human HDGFX nucleotide sequence shown in any of SEQ ID NO:1, it will be appreciated by those skilled in the art that DNA sequence polymorphisms that lead to changes in the amino acid sequences of a HDGFX may exist within a population (e.g., the human population). Such genetic polymorphism in the HDGFX gene may exist among individuals within a population due to natural allelic variation. As used herein, the terms "gene" and "recombinant gene" refer to nucleic acid molecules comprising an open reading frame encoding a HDGFX protein, preferably a mammalian HDGFX protein. Such natural allelic variations can typically result in 1–5% variance in the nucleotide sequence of the HDGFX gene. Any and all such nucleotide variations and resulting amino acid polymorphisms in the HDGFX gene that are the result of natural allelic variation and that do not alter the functional activity of the HDGFX polypeptide are intended to be within the scope of the invention.

Moreover, nucleic acid molecules encoding HDGFX proteins from other species, and thus that have a nucleotide sequence that differs from the human sequence of SEQ ID NO:1, are intended to be within the scope of the invention. Nucleic acid molecules corresponding to natural allelic variants and homologues of the HDGFX cDNAs of the invention can be isolated based on their homology to the human HDGFX nucleic acids disclosed herein using the human cDNAs, or a portion thereof, as a hybridization probe according to standard hybridization techniques under stringent hybridization conditions.

In another embodiment, an isolated nucleic acid molecule of the invention is at least 6 nucleotides in length and hybridizes under stringent conditions to the nucleic acid molecule comprising the nucleotide sequence of SEQ ID NO:1. In another embodiment, the nucleic acid is at least 10, 25, 50, 100, 250, 500 or 750 nucleotides in length. In another embodiment, an isolated nucleic acid molecule of the invention hybridizes to the coding region. As used herein, the term "hybridizes under stringent conditions" is intended to describe conditions for hybridization and washing under which nucleotide sequences that exceed a minimum degree of similarity to each other typically remain hybridized to each other. For example, depending on the degree of stringency imposed, nucleotide sequences at least about 60% similar to each other may hybridize.

As used herein, the phrase "stringent hybridization conditions" refers to conditions under which a probe, primer or oligonucleotide will hybridize to a target sequence; optimally the probe will hybridize to no other sequences, and more generally will not hybridize to sequences below a specified degree of similarity to the probe. Stringent conditions are sequence-dependent and will be different in different circumstances. Longer sequences hybridize specifically at higher temperatures than shorter sequences. Generally, stringent conditions are selected to be about 5° C. lower than the thermal melting point ($T_m$) for the specific sequence at a defined ionic strength and pH. The $T_m$ is the temperature (under defined ionic strength, pH and nucleic acid concentration) at which 50% of the probes complementary to the target sequence hybridize to the target sequence at equilibrium. Since the target sequences are generally present at excess, at $T_m$, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (erg., 10 nt to 50 nt) and at least about 60° C. for longer probes, primers and oligonucleotides. Stringent conditions may also be achieved with the addition of destabilizing agents, such as formamide.

Stringent conditions such as described above are known to those skilled in the art and can be found in CURRENT PROTOCOLS IN MOLECULAR BIOLOGY, John Wiley & Sons, N.Y. (1989), 6.3.1–6.3.6. Preferably, the conditions are such that sequences at least about 65%, 70%, 75%, 85%, 90%, 95%, 98%, or 99% identical to each other typically remain hybridized to each other. A non-limiting example of stringent hybridization conditions is hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C. This hybridization is followed by one or more washes in 0.2×SSC, 0.01% BSA at 50° C. An isolated nucleic acid molecule of the invention that hybridizes under stringent conditions to the sequence of SEQ ID NO:1 corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein).

Homologs (i.e., nucleic acids encoding HDGFX proteins derived from species other than human) or other related sequences (e.g., paralogs) can be obtained by low, moderate or high stringency hybridization with all or a portion of the particular human sequence as a probe using methods well known in the art for nucleic acid hybridization and cloning.

In a second embodiment, a nucleic acid sequence that is hybridizable to the nucleic acid molecule comprising the nucleotide sequence of SEQ ID NO:1, or fragments, analogs or derivatives thereof, under conditions of moderate stringency is provided. A non-limiting example of moderate stringency hybridization conditions are hybridization in 6×SSC, 5×Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well known in the art. See, e.g., Ausubel et al. (eds.), 1993, CURRENT PROTOCOLS IN MOLECULAR BIOLOGY, John Wiley & Sons, NY, and Kriegler, 1990, GENE TANSFER AND EXPRESSION, A LABORATORY MANUAL, Stockton Press, NY.

In a third embodiment, a nucleic acid that is hybridizable to the nucleic acid molecule comprising the nucleotide sequence of SEQ ID NO:1, or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY; Shilo and Weinberg, 1981, *Proc Natl Acad Sci USA* 78: 6789–6792.

Conservative Mutations

In addition to naturally-occurring allelic variants of a HDGFX nucleotide sequence, e.g., a gene sequence, that may exist in the population, the skilled artisan will further appreciate that changes can be introduced by mutation into the nucleotide sequence of SEQ ID NO:1, thereby leading to changes in the amino acid sequence of the encoded HDGFX protein, without altering the functional ability of the HDGFX protein. For example, nucleotide substitutions leading to amino acid substitutions at "non-essential" amino acid residues can be made in the sequence of SEQ ID NO:1. A "non-essential" amino acid residue is a residue at a position in the sequence that can be altered from the wild-type sequence of the HDGFX polypeptide without altering the biological activity, whereas an "essential" amino acid residue is a residue at a position that is required for biological activity. For example, amino acid residues that are conserved among members of a family of HDGFX proteins, of which the HDGFX proteins of the present invention are members, are predicted to be particularly unamenable to alteration.

For example, a HDGFX protein according to the present invention can contain at least one domain that is a typically conserved region in a HDGFX protein family member. As such, these conserved domains are not likely to be amenable to mutation. Other amino acid residues, however, (e.g., those that are poorly conserved among members of the HDGFX protein family) may not be as essential for activity and thus are more likely to be amenable to alteration.

Another aspect of the invention pertains to nucleic acid molecules encoding HDGFX proteins that contain changes in amino acid residues relative to the amino acid sequence of SEQ IDNO:2 that are not essential for activity. In one embodiment, the isolated nucleic acid molecule comprises a nucleotide sequence encoding a protein, wherein the protein comprises an amino acid sequence at least about 75% similar to the amino acid sequence of SEQ ID NO:2. Preferably, the protein encoded by the nucleic acid is at least about 80% identical to any of SEQ ID NO:2, more preferably at least about 90%, 95%, 98%, and most preferably at least about 99% identical to SEQ ID NO:2.

An isolated nucleic acid molecule encoding a protein homologous to the protein of SEQ ID NO:2 can be created by introducing one or more nucleotide substitutions, additions or deletions into the corresponding nucleotide sequence, such that one or more amino acid substitutions, additions or deletions are introduced into the encoded protein.

Mutations can be introduced into SEQ ID NO:1 by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain. Families of amino acid residues having similar side chains have been defined in the art. Certain amino acids have side chains with more than one classifiable characteristic. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, tryptophan, cysteine), nonpolar side chains (e.g., alanine, valine, leucine, isoleucine, proline, phenylalanine, methionine, tyrosine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a HDGFX polypeptide is replaced with another amino acid residue from the same side chain family. Alternatively, in another embodiment, mutations can be introduced randomly along all or part of a HDGFX coding sequence, such as by saturation mutagenesis, and the resultant mutants can be screened for HDGFX polypeptide biological activity to identify mutants that retain activity. Following mutagenesis of SEQ ID NO:1 the encoded protein can be expressed by any recombinant technology known in the art and the activity of the protein can be determined.

The relatedness of amino acid families may also be determined based on side chain interactions. Substituted amino acids may be fully conserved "strong" residues or fully conserved "weak" residues. The "strong" group of conserved amino acid residues may be any one of the following groups: STA, NEQK, NHQK, NDEQ, QHRK, MILV, MILF, HY, FYW, wherein the single letter amino acid codes are grouped by those amino acids that may be substituted for each other. Likewise, the "weak" group of conserved residues may be any one of the following: CSA, ATV, SAG, STNK, STPA, SGND, SNDEQK, NDEQHK, NEQHRK, VLIM, HFY.

Antisense HDGFX Nucleic Acids

Another aspect of the invention pertains to isolated antisense nucleic acid molecules that are hybridizable to or complementary to a HDGFX nucleic acid, e.g., the antisense nucleic acid can be complementary to a nucleic acid molecule comprising the nucleotide sequence of SEQ ID NO: 1, or fragments, analogs or derivatives thereof. An "antisense" nucleic acid includes a nucleotide sequence that is complementary to a "sense" nucleic acid encoding a protein, e.g., complementary to the coding strand of a double-stranded cDNA molecule or complementary to an mRNA sequence. In specific aspects, antisense nucleic acid molecules are provided that comprise a sequence complementary to at least about 10, 25, 50, 100, 250 or 500 nucleotides or an entire HDGFX coding strand, or to only a portion thereof. Nucleic acid molecules encoding fragments, homologs, derivatives and analogs of a HDGFX protein of SEQ ID NO:2 or antisense nucleic acids complementary to a HDGFX nucleic acid sequence of SEQ ID NO:1 are additionally provided.

In one embodiment, an antisense nucleic acid molecule is antisense to a "coding region" of the coding strand of a nucleotide sequence encoding a HDGFX polypeptide. The term "coding region" refers to the region of the nucleotide sequence comprising codons which are translated into amino acid residues (e.g., the protein coding region of a HDGFX polypeptide that corresponds to any of SEQ ID NO:2). In another embodiment, the antisense nucleic acid molecule is antisense to a "noncoding region" of the coding strand of a nucleotide sequence encoding a HDGFX polypeptide. The term "noncoding region" refers to 5' and 3' sequences which flank the coding region that are not translated into amino acids (i.e., also referred to as 5' and 3' untranslated regions).

The HDGFX coding strand sequences disclosed herein (e.g., SEQ ID NO:1) allow for antisense nucleic acids to be designed according to the rules of Watson and Crick or Hoogsteen base pairing. The antisense nucleic acid molecule can be complementary to the entire coding region of a HDGFX mRNA. Alternatively, the antisense nucleic acid molecule can be an oligonucleotide that is antisense to only a portion of the coding or noncoding region of a HDGFX mRNA. For example, the antisense oligonucleotide can be complementary to the region surrounding the translation start site of the HDGFX mRNA. An antisense oligonucleotide can be, for example, about 5, 10, 15, 20, 25, 30, 35, 40, 45 or 50 nucleotides in length.

An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a HDGFX protein to thereby inhibit expression of the protein, e.g., by inhibiting transcription and/or translation. The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of antisense molecules, vector constructs in which the antisense nucleic acid molecule is placed under the control of a strong pol II or pol III promoter are generally preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids Res 15: 6625–6641). The antisense nucleic acid molecule can also comprise a 2'-O-methylribonucleotide (Inoue et al. (1987) Nucleic Acids Res 15: 6131–6148) or a chimeric RNA-DNA analogue (Inoue et al. (1987) FEBS Lett 215: 327–330).

Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject.

Also within the invention is a HDGFX ribozymes. Ribozymes are catalytic RNA molecules with ribonuclease activity that are capable of cleaving a single-stranded nucleic acid, such as a HDGFX mRNA, to which they have a complementary region. Thus, ribozymes (e.g., hammerhead ribozymes (described in Haselhoff and Gerlach (1988) *Nature* 334:585–591)) can be used to catalytically cleave the HDGFX mRNA transcripts to thereby inhibit translation of the HDGFX mRNA. A ribozyme having specificity for a HDGFX-encoding nucleic acid can be designed based upon the nucleotide sequence of a HDGFX nucleic acid disclosed herein (i.e., SEQ ID NO:1). For example, a derivative of a Tetrahymena L-19 IVS RNA can be constructed in which the nucleotide sequence of the active site is complementary to the nucleotide sequence to be cleaved in a HDGFX-encoding mRNA. See, e.g., Cech et al., U.S. Pat. No. 4,987,071; and Cech et al. U.S. Pat. No. 5,116,742. Alternatively, a HDGFX mRNA can be used to select a catalytic RNA having a specific ribonuclease activity from a pool of RNA molecules. See, e.g., Bartel et al., (1993) *Science* 261:1411–1418.

Alternatively, HDGFX gene expression can be inhibited by targeting nucleotide sequences complementary to the regulatory region of a HDGFX gene (e.g., the HDGFX gene promoter and/or enhancers) to form triple helical structures that prevent transcription of the HDGFX gene in target cells. See generally, Helene. (1991) *Anticancer Drug Des.* 6: 569–84; Helene. et al. (1992) *Ann. N.Y. Acad. Sci.* 660:27–36; and Maher (1992) *Bioassays* 14: 807–15.

In various embodiments, the HDGFX nucleic acids can be modified at the base moiety, sugar moiety or phosphate backbone to improve, e.g., the stability, hybridization, or solubility of the molecule. For example, the deoxyribose-phosphate backbone of the nucleic acids can be modified to generate peptide nucleic acids (see Hyrup et al. (1996) *Bioorg Med Chem* 4: 5–23). As used herein, the terms "peptide nucleic acids" or "PNAs" refer to nucleic acid mimics, e.g., DNA mimics, in which the deoxyribosephosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) above; Perry-O'Keefe et al. (1996) *Proc. Nat. Acad. Sci.* (USA) 93: 14670–675.

PNAs based on HDGFX nucleic acids can be used in therapeutic and diagnostic applications. For example, PNAs can be used as antisense or antigene agents for sequence-specific modulation of gene expression by, e.g., inducing transcription or translation arrest or inhibiting replication. PNA based on HDGFX nucleic acids can also be used, e.g., in the analysis of single base pair mutations in a gene by, e.g., PNA directed PCR clamping; as artificial restriction enzymes when used in combination with other enzymes, e.g., S1 nucleases (Hyrup B. (1996) above); or as probes or primers for DNA sequence and hybridization (Hyrup et al. (1996), above; Perry-O'Keefe (1996), above).

In a further embodiment, PNAs of HDGFX nucleic acids can be modified, e g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of the nucleic acids can be generated that may combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) above). The synthesis of PNA-DNA chimeras can be performed as described in Hyrup (1996) above and Finn et al. (1996) *Nucl Acids Res* 24: 3357–63. For example, a DNA chain can be synthesized on a solid support using standard phosphoramidite coupling chemistry, and modified nucleoside analogs, e.g., 5'-(4-methoxytrityl)amino-5'-deoxy-thymidine phosphoramidite, can be used between the PNA and the 5' end of DNA (Mag et al. (1989) *Nucl Acid Res* 17: 5973–88). PNA monomers are then coupled in a stepwise manner to produce a chimeric molecule with a 5' PNA segment and a 3' DNA segment (Finn et al. (1996) above). Alternatively, chimeric molecules can be synthesized with a 5' DNA segment and a 3' PNA segment. See, Petersen et al. (1975) *Bioorg Med Chem Lett* 5: 1119–11124.

In other embodiments, a HDGFX nucleic acid or antisense nucleic acid may include other appended groups such as peptides (e.g., for targeting host cell receptors in vivo), or agents facilitating transport across the cell membrane (see, e.g., Letsinger et al., 1989, *Proc. Natl. Acad. Sci. U.S.A.* 86:6553–6556; Lemaitre et al., 1987, *Proc. Natl. Acad. Sci.* 84:648–652; PCT Publication No. WO88/09810) or the blood-brain barrier (see, e.g., PCT Publication No. WO89/10134). In addition, oligonucleotides can be modified with hybridization triggered cleavage agents (See, e.g., Krol et al., 1988, *BioTechniques* 6:958–976) or intercalating agents. (See, e.g., Zon, 1988, *Pharm. Res.* 5: 539–549). To this end, the oligonucleotide may be conjugated to another molecule, e.g., a peptide, a hybridization triggered cross-linking agent, a transport agent, a hybridization-triggered cleavage agent, etc.

HDGFX Polypeptides

A HDGFX polypeptide of the invention includes a protein whose sequence is provided in SEQ ID NO:2. The invention also includes a mature form of a HDGFX polypeptide, as well as a mutant or variant form of a HDGFX polypeptide. In some embodiments, a mutant or variant HDGFX includes a protein in which any residues may be changed from the corresponding residue shown in Table 1, while still encoding a protein that maintains its HDGFX-like activities and physiological functions, or a functional fragment thereof. The invention includes the polypeptides encoded by the variant HDGFX nucleic acids described above. In the mutant or variant protein, up to 20% or more of the residues may be so changed.

In general, a HDGFX polypeptide variant that preserves HDGFX function includes any HDGFX polypeptide variant in which residues at a particular position in the sequence have been substituted by other amino acids. A HDGFX variant polypeptide also includes a HDGFX polypeptide in which an additional residue or residues has been inserted between two residues of the parent protein as well as a protein in which one or more residues have been deleted from a reference HDGFX polypeptide sequence (e.g., SEQ ID NO:2, or a mature form of SEQ ID NO:2). Thus, any amino acid substitution, insertion, or deletion with respect to a reference HDGFX polypeptide sequence (e.g., SEQ ID NO:2, or a mature form of SEQ ID NO:2) is encompassed by the invention. In some embodiments, a mutant or variant proteins may include one or more substitutions, insertions, or deletions with respect to a reference HDGFX sequence.

The invention also includes isolated HDGFX proteins, and biologically active portions thereof, or derivatives, fragments, analogs or homologs thereof. Also provided are polypeptide fragments suitable for use as immunogens to raise anti-HDGFX antibodies. In one embodiment, native HDGFX proteins can be isolated from cells or tissue sources by an appropriate purification scheme using standard protein purification techniques. In another embodiment, HDGFX proteins are produced by recombinant DNA techniques. Alternative to recombinant expression, a HDGFX protein or polypeptide can be synthesized chemically using standard peptide synthesis techniques.

An "isolated" or "purified" protein or biologically active portion thereof is substantially free of cellular material or other contaminating proteins from the cell or tissue source from which the HDGFX protein is derived, or substantially free from chemical precursors or other chemicals when chemically synthesized. The language "substantially free of cellular material" includes preparations of a HDGFX protein in which the protein is separated from cellular components of the cells from which it is isolated or recombinantly produced. In one embodiment, the language "substantially free of cellular material" includes preparations of a HDGFX protein having less than about 30% (by dry weight) of non-HDGFX protein (also referred to herein as a "contaminating protein"), more preferably less than about 20% of non-HDGFX protein, still more preferably less than about 10% of non-HDGFX protein, and most preferably less than about 5% non-HDGFX protein. When the HDGFX protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of a HDGFX protein in which the protein is separated from chemical precursors or other chemicals that are involved in the synthesis of the protein. In one embodiment, the language "substantially free of chemical precursors or other chemicals" includes preparations of a HDGFX protein having less than about 30% (by dry weight) of chemical precursors or non HDGFX polypeptides, more preferably less than about 20% chemical precursors or non-HDGFX polypeptides, still more preferably less than about 10% chemical precursors or non-HDGFX polypeptides, and most preferably less than about 5% chemical precursors or non-HDGFX polypeptides.

Biologically active portions of a HDGFX protein include peptides comprising amino acid sequences sufficiently homologous to or derived from the amino acid sequence of the HDGFX protein, e.g., the amino acid sequence shown in SEQ ID NO:2 that include fewer amino acids than the full length HDGFX proteins, and exhibit at least one activity of a HDGFX protein. Typically, biologically active portions comprise a domain or motif with at least one activity of the HDGFX protein. A biologically active portion of a HDGFX protein can be a polypeptide which is, for example, 10, 25, 50, 100 or more amino acids in length.

A biologically active portion of a HDGFX of the present invention may contain at least one of the above-identified domains conserved among the HDGFX family of proteins. Moreover, other biologically active portions, in which other regions of the protein are deleted, can be prepared by recombinant techniques and evaluated for one or more of the functional activities of a native HDGFX protein.

In some embodiments, the HDGFX protein is substantially homologous to any of SEQ ID NO:2 and retains the functional activity of the protein of SEQ ID NO:2, yet differs in amino acid sequence due to natural allelic variation or mutagenesis, as described in detail below. Accordingly, in another embodiment, the HDGFX protein is a protein that comprises an amino acid sequence at least about 45% homologous, and more preferably about 55, 65, 70, 75, 80, 85, 90, 95, 98 or even 99% homologous to the amino acid sequence of SEQ ID NO:2 and retains the functional activity of the HDGFX proteins of the corresponding polypeptide having the sequence of SEQ ID NO:2.

Determining Homology Between Two or More Sequences

To determine the percent homology of two amino acid sequences or of two nucleic acids, the sequences are aligned for optimal comparison purposes (e.g., gaps can be introduced in either of the sequences being compared for optimal alignment between the sequences). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See, Needleman and Wunsch 1970 *J Mol Biol* 48: 443–453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of the DNA sequence shown in SEQ ID NO:1. Equivalent software procedures for determining the extent of sequence identity are widely known in the art may be used in the present context.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T or U, C, G, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region. The term "percentage of positive residues" is calculated by comparing two optimally aligned sequences over that region of comparison, determining the number of positions at which the identical and conservative amino acid substitutions, as defined above, occur in both sequences to yield the number of matched positions, dividing the number

Chimeric and Fusion HDGFX Proteins

The invention also provides HDGFX chimeric or fusion proteins. As used herein, a HDGFX "chimeric protein" or "fusion protein" includes a HDGFX polypeptide operatively linked to a non-HDGFX polypeptide. A "HDGFX polypeptide" refers to a polypeptide having an amino acid sequence corresponding to a HDGFX polypeptide, or a fragment, variant or derivative thereof, whereas a "non-HDGFX polypeptide" refers to a polypeptide having an amino acid sequence corresponding to a protein that is not substantially homologous to the HDGFX protein, e.g., a protein that is different from the HDGFX protein and that is derived from the same or a different organism. Thus, within a HDGFX fusion protein, the HDGFX polypeptide can correspond to all or a portion of a HDGFX protein. In one embodiment, a HDGFX fusion protein comprises at least one biologically active portion of a HDGFX protein. In another embodiment, a HDGFX fusion protein comprises at least two biologically active portions of a HDGFX protein. Within the fusion protein, the term "operatively linked" is intended to indicate that the HDGFX polypeptide and the non-HDGFX polypeptide are fused in-frame to each other. The non-HDGFX polypeptide can be fused to the N-terminus or C-terminus of the HDGFX polypeptide.

For example, in one embodiment a HDGFX fusion protein comprises a HDGFX polypeptide operably linked to the extracellular domain of a second protein. Such fusion proteins can be further utilized in screening assays for compounds that modulate HDGFX activity (such assays are described in detail below).

In another embodiment, the fusion protein is a GST-HDGFX fusion protein in which the HDGFX sequences are fused to the C-terminus of the GST (i.e., glutathione S-transferase) sequences. Such fusion proteins can facilitate the purification of recombinant HDGFX.

In yet another embodiment, the fusion protein is a HDGFX protein containing a heterologous signal sequence at its N-terminus. For example, the native HDGFX signal sequence can be removed and replaced with a signal sequence from another protein. In certain host cells (e.g., mammalian host cells), expression and/or secretion of the HDGFX can be increased through use of a heterologous signal sequence.

In a further embodiment, the fusion protein is a HDGFX-immunoglobulin fusion protein in which the HDGFX sequences comprising one or more domains are fused to sequences derived from a member of the immunoglobulin protein family. The HDGFX-immunoglobulin fusion proteins of the invention can be incorporated into pharmaceutical compositions and administered to a subject to inhibit an interaction between a HDGFX ligand and a HDGFX protein on the surface of a cell, to thereby suppress HDGFX-mediated signal transduction in vivo. In one example, a contemplated HDGFX ligand of the invention is a HDGFX receptor. The HDGFX-immunoglobulin fusion proteins can be used to modulate the bioavailability of a HDGFX cognate ligand. Inhibition of the HDGFX ligand/HDGFX interaction may be useful therapeutically for both the treatment of proliferative and differentiative disorders, as well as modulating (e.g., promoting or inhibiting) cell survival. Moreover, the HDGFX-immunoglobulin fusion proteins of the invention can be used as immunogens to produce anti-HDGFX antibodies in a subject, to purify HDGFX ligands, and in screening assays to identify molecules that inhibit the interaction of a HDGFX with a HDGFX ligand. A HDGFX chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). A HDGFX-encoding nucleic acid can be cloned into such an expression vector such that the fusion moiety is linked in-frame to the HDGFX protein.

HDGFX Agonists And Antagonists

The present invention also pertains to variants of a HDGFX protein that function as either HDGFX agonists (mimetics) or as HDGFX antagonists. Variants of a HDGFX protein can be generated by mutagenesis, e.g., discrete point mutation or truncation of the HDGFX protein. An agonist of the HDGFX protein can retain substantially the same, or a subset of, the biological activities of the naturally occurring form of the HDGFX protein. An antagonist of the HDGFX protein can inhibit one or more of the activities of the naturally occurring form of the HDGFX protein by, for example, competitively binding to a downstream or upstream member of a cellular signaling cascade which includes the HDGFX protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the HDGFX protein.

Variants of the HDGFX protein that function as either HDGFX agonists (mimetics) or as HDGFX antagonists can be identified by screening combinatorial libraries of mutants, e.g., truncation mutants, of the HDGFX protein for HDGFX protein agonist or antagonist activity. In one embodiment, a variegated library of HDGFX variants is generated by combinatorial mutagenesis at the nucleic acid level and is encoded by a variegated gene library. A variegated library of HDGFX variants can be produced by, for example, enzymatically ligating a mixture of synthetic oligonucleotides into gene sequences such that a degenerate set of potential HDGFX sequences is expressible as individual polypeptides, or alternatively, as a set of larger fusion proteins (e.g., for phage display) containing the set of HDGFX sequences therein. There are a variety of methods which can be used to produce libraries of potential HDGFX variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential HDGFX variant sequences. Methods for synthesizing degenerate oligonucleotides are known in the art (see, e.g., Narang (1983) *Tetrahedron* 39:3; Itakura et al. (1984) *Annu Rev Biochem* 53:323; Itakura et al. (1984) *Science* 198:1056; Ike et al. (1983) *Nucl Acid Res* 11:477.

Polypeptide Libraries

In addition, libraries of fragments of the HDGFX protein coding sequence can be used to generate a variegated population of growth promoter fragments for screening and subsequent selection of variants of a HDGFX protein. In one embodiment, a library of coding sequence fragments can be generated by treating a double stranded PCR fragment of a HDGFX coding sequence with a nuclease under conditions wherein nicking occurs only about once per molecule, denaturing the double stranded DNA, renaturing the DNA to form double stranded DNA that can include sense/antisense pairs from different nicked products, removing single stranded portions from reformed duplexes by treatment with S 1 nuclease, and ligating the resulting fragment library into an expression vector. By this method, an expression library can be derived which encodes N-terminal and internal fragments of various sizes of the HDGFX protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of HDGFX proteins. The most widely used techniques, which are amenable to high throughput analysis, for screening large gene libraries typically include cloning the gene library into replicable expression vectors, transforming appropriate cells with the resulting library-of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify HDGFX variants (Arkin and Yourvan (1992) PNAS 89:7811–7815; Delgrave et al. (1993) Protein Engineering 6:327–331).

Anti-HDGFX Antibodies

The term "antibody" as used herein refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, and an $F_{ab}$ expression library. In general, antibody molecules obtained from humans to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

An isolated protein of the invention intended to serve as an antigen, or a portion or fragment thereof, can be used as an immunogen to generate antibodies that immunospecifically bind the antigen, using standard techniques for polyclonal and monoclonal antibody preparation. The full-length protein can be used or, alternatively, the invention provides antigenic peptide fragments of the antigen for use as immunogens. An antigenic peptide fragment comprises at least 6 amino acid residues of the amino acid sequence of the full length protein, such as an amino acid sequence shown in SEQ ID NO:2, and encompasses an epitope thereof such that an antibody raised against the peptide forms a specific immune complex with the full length protein or with any fragment that contains the epitope. Preferably, the antigenic peptide comprises at least 10 amino acid residues, or at least 15 amino acid residues, or at least 20 amino acid residues, or at least 30 amino acid residues. Preferred epitopes encompassed by the antigenic peptide are regions of the protein that are located on its surface; commonly these are hydrophilic regions.

In certain embodiments of the invention, at least one epitope encompassed by the antigenic peptide is a region of the HDGFX that is located on the surface of the protein, e.g., a hydrophilic region. A hydrophobicity analysis of the human HDGFX protein sequence will indicate which regions of a HDGFX polypeptide are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, *Proc. Nat. Acad. Sci. USA* 78: 3824–3828; Kyte and Doolittle 1982, *J. Mol. Biol.* 157: 105–142, each incorporated herein by reference in their entirety. Antibodies that are specific for one or more domains within an antigenic protein, or derivatives, fragments, analogs or homologs thereof, are also provided herein.

As disclosed herein, HDGFX protein sequence of SEQ ID NO:2, or derivatives, fragments, analogs or homologs thereof, may be utilized as immunogens in the generation of antibodies that immunospecifically-bind these protein components. The term "antibody" as used herein refers to immunoglobulin molecules and immunologically active portions of immunoglobulin molecules, i.e., molecules that contain an antigen binding site that specifically binds (immunoreacts with) an antigen, such as HDGFX. Such antibodies include, but are not limited to, polyclonal, monoclonal, chimeric, single chain, $F_{ab}$ and $F_{(ab')2}$ fragments, and an $F_{ab}$ expression library. In a specific embodiment, antibodies to human HDGFX proteins are disclosed. Various procedures known within the art may be used for the production of polyclonal or monoclonal antibodies to a HDGFX protein sequence of SEQ ID NO:2, or a derivative, fragment, analog or homolog thereof. Some of these proteins are discussed below.

In one embodiment, methods for the screening of antibodies that possess the desired specificity include, but are not limited to, enzyme-linked immunosorbent assay (ELISA) and other immunologically-mediated techniques known within the art. In a specific embodiment, selection of antibodies that are specific to a particular domain of a HDGFX protein is facilitated by generation of hybridomas that bind to the fragment of a HDGFX protein possessing such a domain. Antibodies that are specific for one or more domains within a HDGFX protein, e.g., the carboxyterminal residues specific to HDGFX when compared to HGDF (see, e.g., Tables 3–4), or derivatives, fragments, analogs or homologs thereof, are also provided herein.

Various procedures known within the art may be used for the production of polyclonal or monoclonal antibodies directed against a protein of the invention, or against derivatives, fragments, analogs homologs or orthologs thereof (see, for example, Antibodies: A Laboratory Manual, Harlow E, and Lane D, 1988, Cold Spring Harbor Laboratory Press, Cold Spring Harbor, N.Y., incorporated herein by reference). Some of these antibodies are discussed below.

Polyclonal Antibodies

For the production of polyclonal antibodies, various suitable host animals (e.g., rabbit, goat, mouse or other mammal) may be immunized by one or more injections with the native protein, a synthetic variant thereof, or a derivative of the foregoing. An appropriate immunogenic preparation can contain, for example, the naturally occurring immunogenic protein, a chemically synthesized polypeptide representing the immunogenic protein, or a recombinantly expressed immunogenic protein. Furthermore, the protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), adjuvants usable in humans such as Bacille Calmette-Guerin and Corynebacterium parvum, or similar immunostimulatory agents. Additional examples of adjuvants which can be employed include MPL-TDM adjuvant (monophosphoryl Lipid A, synthetic trehalose dicorynomycolate).

The polyclonal antibody molecules directed against the immunogenic protein can be isolated from the mammal (e.g., from the blood) and further purified by well known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25–28).

Monoclonal Antibodies

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen binding site capable of immunoreacting with a particular epitope of the antigen characterized by a unique binding affinity for it.

Monoclonal antibodies can be prepared using hybridoma methods, such as those described in the art. See, e.g., Kohler and Milstein, 1975 Nature, 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, MONOCLONAL ANTIBODIES: PRINCIPLES AND PRACTICE, Academic Press, (1986) pp. 59–103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. See, e.g. Kozbor 1984 J. Immunol., 133:3001; Brodeur et al. MONOCLONAL ANTIBODY PRODUCTION TECHNIQUES AND APPLICATIONS, Marcel Dekker, Inc., New York, (1987) pp. 51–63.

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis. See, e.g. Munson and Pollard 1980 Anal. Biochem. 107: 220. It is an objective, especially important in therapeutic applications of monoclonal antibodies, to identify antibodies having a high degree of specificity and a high binding affinity for the target antigen.

After the desired hybridoma cells are identified, the clones can be subcloned by limiting dilution procedures and grown by standard methods (Goding,1986). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison, *Nature* 368, 812–13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Humanized Antibodies

The antibodies directed against the protein antigens of the invention can further comprise humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al., *Nature*, 321:522–525 (1986); Riechmann et al., *Nature*, 332:323–327 (1988); Verhoeyen et al., *Science*, 239:1534–1536 (1988)), by substituting rodent CDRs or CDR sequences for the corresponding sequences of a human antibody. (See also U.S. Pat. No. 5,225,539.) In some instances, Fv framework residues of the human immunoglobulin are replaced by corresponding non-human residues. Humanized antibodies can also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986; Riechmann et al., 1988; and Presta, *Curr. Op. Struct. Biol.*, 2:593–596 (1992)).

Human Antibodies

Fully human antibodies essentially relate to antibody molecules in which the entire sequence of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77–96). Human monoclonal antibodies may be utilized in the practice of the present invention and may be produced by using human hybridomas (see Cote, et al., 1983. Proc Natl Acad Sci USA 80: 2026–2030) or by transforming human B-cells with Epstein Barr Virus in vitro (see Cole, et al., 1985 In: MONOCLONAL ANTIBODIES AND CANCER THERAPY, Alan R. Liss, Inc., pp. 77–96).

In addition, human antibodies can also be produced using additional techniques, including phage display libraries (Hoogenboom and Winter, *J. Mol. Biol.*, 227:381 (1991); Marks et al., *J. Mol. Biol.*, 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (*Bio/Technology* 10, 779–783 (1992)); Lonberg et al. (*Nature* 368 856–859 (1994)); Morrison (*Nature* 368, 812–13 (1994)); Fishwild et al,(*Nature Biotechnology* 14, 845–51 (1996)); Neuberger (*Nature Biotechnology* 14, 826 (1996)); and Lonberg and Huszar (*Intern. Rev. Immunol.* 13 65–93 (1995)).

Human antibodies may additionally be produced using transgenic nonhuman animals which are modified so as to produce fully human antibodies rather than the animal's endogenous antibodies in response to challenge by an antigen. (See publication WO 94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

$F_{ab}$ Fragments and Single Chain Antibodies

Techniques can be adapted for the production of single-chain antibodies specific to an antigenic protein of the invention (see e.g., U.S. Pat. No. 4,946,778). In addition, methods can be adapted for the construction of Fab expression libraries (see e.g., Huse, et al., 1989 Science 246: 1275–1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537–539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., EMBO J., 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from E. coli and chemically coupled to form bispecific antibodies. Shalaby et al., J. Exp. Med. 175:217–225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic. activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two-antigen-binding sites. Another strategy for making bispecific antibody fragments by the use of single-chain Fv (sFv) dimers has also been reported. See, Gruber et al., *J. Immunol.* 152:5368 (1994).

Antibodies with more than two valencies are contemplated. For example, trispecific antibodies can be prepared. Tutt et al., *J. Immunol.* 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

Effector Function Engineering

It can be desirable to modify the antibody of the invention with respect to effector function, so as to enhance, erg, the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). See Caron et al., *J. Exp Med.*, 176: 1191–1195 (1992) and Shopes, *J. Immunol.*, 148: 2918–2922 (1992). Homodimeric antibodies with enhanced anti-tumor activity can also be prepared using heterobifunctional cross-linkers as described in Wolff et al. *Cancer Research*, 53: 2560–2565 (1993). Alternatively, an antibody can be engineered that has dual Fc regions and can thereby have enhanced complement lysis and ADCC capabilities. See Stevenson et al., *Anti-Cancer Drug Design*, 3: 219–230 (1989).

Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody can be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is in turn conjugated to a cytotoxic agent.

Immunoliposomes

The antibodies disclosed herein can also be formulated as immunoliposomes. Liposomes containing the antibody are prepared by methods known in the art, such as described in Epstein et al., *Proc. Natl. Acad. Sci. USA*, 82: 3688 (1985); Hwang et al., *Proc. Natl Acad. Sci. USA*, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising .phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.*, 257: 286–288 (1982) via a disulfide-interchange reaction. A chemotherapeutic agent (such as Doxorubicin) is optionally contained within the liposome. See Gabizon et al., *J. National Cancer Inst.*, 81(19): 1484 (1989).

Diagnostic Applications of Antibodies Directed Against the Proteins of the Invention Antibodies directed against a protein of the invention may be used in methods known within the art relating to the localization and/or quantitation of the protein (e.g., for use in measuring levels of the protein within appropriate physiological samples, for use in diagnostic methods, for use in imaging the protein, and the like). In a given embodiment, antibodies against the proteins, or derivatives, fragments, analogs or homologs thereof, that contain the antigen binding domain, are utilized as pharmacologically-active compounds (see below).

An antibody specific for a protein of the invention can be used to isolate the protein by standard techniques, such as immunoaffinity chromatography or immunoprecipitation. Such an antibody can facilitate the purification of the natural protein antigen from cells and of recombinantly produced antigen expressed in host cells. Moreover, such an antibody can be used to detect the antigenic protein (e.g., in a cellular lysate or cell supernatant) in order to evaluate the abundance and pattern of expression of the antigenic protein. Antibodies directed against the protein can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidinibiotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^3$H.

Pharmaceutical Compositions of Antibodies

Antibodies specifically binding a protein of the invention, as well as other molecules identified by the screening assays disclosed herein, can be administered for the treatment of various disorders in the form of pharmaceutical compositions. Principles and considerations involved in preparing such compositions, as well as guidance in the choice of components are provided, for example, in Remington: THE SCIENCE AND PRACTICE OF PHARMACY 19th ed. (Alfonso R. Gennaro, et al., editors) Mack Pub. Co., Easton, Pa. 1995; DRUG ABSORPTION ENHANCEMENT: CONCEPTS, POSSIBILITIES, LIMITATIONS, AND TRENDS, Harwood Academic i Publishers, Langhorne, Pa., 1994; and PEPTIDE AND PROTEIN DRUG DELIVERY (Advances In Parenteral Sciences, Vol. 4), 1991, M. Dekker, New York.

If the antigenic protein is intracellular and whole antibodies are used as inhibitors, internalizing antibodies are preferred. However, liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., Proc. Natl. Acad. Sci. USA, 90: 7889–7893 (1993). The formulation herein can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Antibody Therapeutics

Antibodies of the invention, including polyclonal, monoclonal, humanized and fully human antibodies, may used as therapeutic agents. Such agents will generally be employed to treat or prevent a disease or pathology in a subject. An antibody preparation, preferably one having high specificity and high affinity for its target antigen, is administered to the subject and will generally have an effect due to its binding with the target. Such an effect may be one of two kinds, depending on the specific nature of the interaction between the given antibody molecule and the target antigen in question. In the first instance, administration of the antibody may abrogate or inhibit the binding of the target with an endogenous ligand to which it naturally binds. In this case, the antibody binds to the target and masks a binding site of the naturally occurring ligand, wherein the ligand serves as an effector molecule. Thus the receptor mediates a signal transduction pathway for which ligand is responsible.

Alternatively, the effect may be one in which the antibody elicits a physiological result by virtue of binding to an effector binding site on the target molecule. In this case the target, a receptor having an endogenous ligand which may be absent or defective in the disease or pathology, binds the antibody as a surrogate effector ligand, initiating a receptor-based signal transduction event by the receptor.

A therapeutically effective amount of an antibody of the invention relates generally to the amount needed to achieve a therapeutic objective. As noted above, this may be a binding interaction between the antibody and its target antigen that, in certain cases, interferes with the functioning of the target, and in other cases, promotes a physiological response. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

HDGFX Recombinant Vectors and Host Cells

Another aspect of the invention pertains to vectors, preferably expression vectors, containing a nucleic acid encoding a HDGFX protein, or derivatives, fragments, analogs or homologs thereof. As used herein, the term "vector" refers to a-nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively linked to the nucleic acid sequence to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., HDGFX proteins, mutant forms of the HDGFX, fusion proteins, etc.).

The recombinant expression vectors of the invention can be designed for expression of a HDGFX nucleic acid in prokaryotic or eukaryotic cells. For example, the HDGFX can be expressed in bacterial cells such as E. coli, insect cells (using baculovirus expression vectors) yeast celis or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example, using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Oftena proteolytic cleavage site is introduced in fusion expression vectors at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31–40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion E. coli expression vectors include pTrc (Amrann et al., (1988) Gene 69:301–315) and pET l Id (Studier et al., GENE EXPRESSION TECHNOLOGY: METHODS IN ENZYMOLOGY 185, Academic Press, San Diego, Calif. (1990) 60–89).

One strategy to maximize recombinant protein expression in E. coli is to express the protein in a host bacteria with an impaired capacity to proteolytically cleave the recombinant protein. See, Gottesman, GENE EXPRESSION TECHNOLOGY: METHODS IN ENZYMOLOGY 185, Academic Press, San Diego, Calif. (1990) 119–128. Another strategy is to alter the nucleic acid sequence of the nucleic acid to be inserted into an expression vector so that the individual codons for each amino acid are those preferentially utilized in E. coli (Wada et al., (1992) *Nucleic Acids Res.* 20:2111–2118). Such alteration of nucleic acid sequences of the invention can be carried out by standard DNA synthesis techniques.

In another embodiment, the HDGFX expression vector is a yeast expression vector. Examples of vectors for expression in yeast S. cerivisae include pYepSec1 (Baldari, et al., (1987) *EMBO J* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, the HDGFX nucleic acid can be expressed in insect cells using baculovirus expression vectors. Baculovirus vectors available for expression of proteins in cultured insect cells (e.g., SF9 cells) include the pAc series (Smith et.al. (1983) *Mol Cell Biol* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufman et al. (1987) *EMBO J* 6: 187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells. See, e.g., Chapters 16 and 17 of Sambrook et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev 1:268–277), lymphoid-specific promoters (Calame and Eaton (1988) Adv Immunol 43:235–275), in particular promoters of T cell receptors (Winoto and Baltimore (1989) EMBO J 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) PNAS 86:5473–5477), pancreas-specific promoters (Edlund et al. (1985) Science 230:912–916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss (1990) Science 249:374–379) and the α-fetoprotein promoter (Campes and Tilghman (1989) Genes Dev 3:537–546).

The invention further provides a recombinant expression vector comprising a DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to a HDGFX mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., "Antisense RNA as a molecular tool for genetic analysis," Reviews—Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, the HDGFX protein can be expressed in bacterial cells such as E. coli, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding the growth promoter or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) the HDGFX protein. Accordingly, the invention further provides methods for producing the HDGFX protein using the host cells of the invention. In one embodiment, the method comprises culturing the host cell of invention (into which a recombinant expression vector encoding the HDGFX polypeptide has been introduced) in a suitable medium such that the HDGFX protein is produced. In another embodiment, the method further comprises isolating the HDGFX from the medium or the host cell.

Transgenic Animals

The host cells of the invention can also be used to produce nonhuman transgenic animals. For example, in one embodiment, a host cell of the invention is a fertilized oocyte or an embryonic stem cell into which HDGFX-coding sequences have been introduced. Such host cells can then be used to create non-human transgenic animals in which exogenous HDGFX sequences have been introduced into their genome or homologous recombinant animals in which endogenous HDGFX sequences have been altered. Such animals are useful for studying the function and/or activity of the HDGFX sequences and for identifying and/or evaluating modulators of HDGFX activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous HDGFX gene has been altered by homologous recombination between the endogenous gene and an exogenous DNA molecule introduced into a cell of the animal, e.g., an embryonic cell of the animal, prior to development of the animal.

A transgenic animal of the invention can be created by introducing HDGFX-encoding nucleic acid into the male pronuclei of a fertilized oocyte, e.g., by microinjection, retroviral infection, and allowing the oocyte to develop in a pseudopregnant female foster animal. The human HDGFX DNA sequence of SEQ ID NO:1 can be introduced as a transgene into the genome of a non-human animal. Alternatively, a nonhuman homologue of the human HDGFX gene, such as a mouse HDGFX gene, can be isolated based on hybridization to the human HDGFX cDNA (described further above) and used as a transgene. Intronic sequences and polyadenylation signals can also be included in the transgene to increase the efficiency of expression of the transgene. A tissue-specific regulatory sequence(s) can be operably linked to the HDGFX transgene to direct expression of HDGFX protein to particular cells. Methods for generating transgenic animals via embryo manipulation and microinjection, particularly animals such as mice, have become conventional in the art and are described, for example, in U.S. Pat. Nos. 4,736,866; 4,870,009; and 4,873,191; and Hogan 1986, In: MANIPULATING THE MOUSE EMBRYO, Cold Spring Harbor Laboratory Press, Cold Spring Harbor, N.Y. Similar methods are used for production of other transgenic animals. A transgenic founder animal can be identified based upon the presence of the HDGFX transgene in its genome and/or expression of HDGFX mRNA in tissues or cells of the animals. A transgenic founder animal can then be used to breed additional animals carrying the transgene. Moreover, transgenic animals carrying a transgene encoding a HDGFX can further be bred to other transgenic animals carrying other transgenes.

To create a homologous recombinant animal, a vector is prepared which contains at least a portion of a HDGFX gene into which a deletion, addition or substitution has been introduced to thereby alter, e.g., functionally disrupt, the HDGFX gene. The HDGFX gene can be a human gene (e.g., SEQ ID NO:1), but more preferably, is a non-human homologue of a human HDGFX gene. For example, a mouse homologue of human HDGFX gene of SEQ ID NO:1 can be used to construct a homologous recombination vector suitable for altering an endogenous HDGFX gene in the mouse genome. In one embodiment, the vector is designed such that, upon homologous recombination, the endogenous HDGFX gene is functionally disrupted (i.e., no longer encodes a functional protein; also referred to as a "knock out" vector).

Alternatively, the vector can be designed such that, upon homologous recombination, the endogenous HDGFX gene is mutated or otherwise altered but still encodes functional protein (e.g., the upstream regulatory region can be altered to thereby alter the expression of the endogenous HDGFX protein). In the homologous recombination vector, the altered portion of the HDGFX gene is flanked at its 5' and 3' ends by additional nucleic acid of the HDGFX gene to allow for homologous recombination to occur between the exogenous HDGFX protein gene carried by the vector and an endogenous HDGFX protein gene in an embryonic stem cell. The additional flanking HDGFX protein nucleic acid is of sufficient length for successful homologous recombination with the endogenous gene. Typically, several kilobases of flanking DNA (both at the 5' and 3' ends) are included in the vector. See e.g., Thomas et al. (1987) Cell 51:503 for a description of homologous recombination vectors. The vector is introduced into an embryonic stem cell line (e.g., by electroporation) and cells in which the introduced HDGFX protein gene has homologously recombined with the endogenous HDGFX protein gene are selected (see. e.g., Li et al. (1992) Cell 69:915).

The selected cells are then injected into a blastocyst of an animal (e.g., a mouse) to form aggregation chimeras. See e.g., Bradley 1987, In: TERATOCARCINOMAS AND EMBRYONIC STEM CELLS: A PRACTICAL APPROACH, Robertson, ed. IRL, Oxford, pp. 113–152. A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) Curr Opin Biotechnol 2:823–829; PCT International Publication Nos.: WO 90/1184; WO 91/01140; WO 92/0968; and WO 93/04169.

In another embodiment, transgenic non-humans animals can be produced that contain selected systems that allow for regulated expression of the transgene. One example of such a system is the cre/loxP recombinase system of bacteriophage P1. For a description of the cre/loxP recombinase system, see, e.g., Lakso et al. (1992) PNAS 89:6232–6236. Another example of a recombinase system is the FLP recombinase system of Saccharomyces cerevisiae (O'Gorman et al. (1991) Science 251:181–185. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) Nature 385:810–813. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

Pharmaceutical Compositions

The HDGFX nucleic acid molecules, HDGFX proteins, and anti-HDGFX antibodies of the invention, and derivatives, fragments, analogs and homologs thereof are designated "active compounds" or "Therapeutics" herein. Additionally, low molecular weight compounds which have the property that they either bind to the HDGFX nucleic acid molecules, the HDGFX proteins, and the anti-HDGFX antibodies of the invention, and derivatives, fragments, analogs and homologs thereof, or induce pharmacological agonist or antagonist responses commonly ascribed to a HDGFX nucleic acid molecule, a HDGFX protein, and derivatives, fragments, analogs and homologs thereof, are also termed "active compounds" or "Therapeutics" herein. These Therapeutics can be incorporated into pharmaceutical compositions suitable for administration to a subject. Such compositions typically comprise the nucleic acid molecule, protein, or antibody and a pharmaceutically acceptable carrier.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a HDGFX protein or anti-HDGFX protein antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can beprepared according to methods known to those skilled in the art, for example, as described in U.S. Pat. No. 4,522,811.

Sustained-release preparations can be prepared. Suitable examples of sustained-release preparations include semipermeable matrices of solid hydrophobic polymers containing the antibody, which matrices are in the form of shaped articles, e.g., films, or microcapsules.

Examples of sustained-release matrices include polyesters, hydrogels (for example, poly(2-thydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release pharmaceutical active agents over shorter time periods.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

The nucleic acid molecules of the invention can be inserted into vectors and used as gene therapy vectors. Gene therapy vectors can be delivered to a subject by any of a number of routes, e.g., as described in U.S. Pat. No. 5,703,055. Delivery can thus also include, e.g., intravenous injection, local administration (see U.S. Pat. No. 5,328,470) or stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a kit, e.g., in a container, pack, or dispenser together with instructions for administration.

Also within the invention is the use of a therapeutic in the manufacture of a medicament for treating a syndrome associated with a human disease, the disease selected from a HDGFX-associated disorder, wherein said therapeutic is selected from the group consisting of a HDGFX polypeptide, a HDGFX nucleic acid, and an anti-HDGFX antibody.

Additional Uses and Methods of the Invention

Various HDGF family members have been implicated in angiogenesis, spermatogenesis, smooth muscle growth and neuronal development. Accordingly, this suggests a role of HDGFX in treating or diagosing disease related to these funtions. For example, HDGF various cancers, coronary artery disease, arthritis, diabetic retinopathy, infertility and various neurological diseases, e.g., Parkinson's Disease, Alzheimer's, amyotropic lateral sclerosis and psychiatric disorders.

The potential role(s) of HDGFX in tumorigenesis may include autocrine stimulation of tumor growth, hormone independence, angiogenesis, metastatic progression, chemoresistance, radiotherapy resistance, survival in trophic factor limited secondary tissue site microenvironments, and stimulation of tumor cell matrix degradation and tumor cell migration (i.e., tumor invasion).

The nucleic acid molecules, proteins, protein homologues, and antibodies described herein can be used in one or more of the following methods: (a) screening assays; (b) detection assays (e.g., chromosomal mapping, cell and tissue typing, forensic biology), (c) predictive medicine (e.g., diagnostic assays, prognostic assays, monitoring clinical trials, and pharmacogenomics); and (d) methods of treatment (e.g., therapeutic and prophylactic).

The isolated nucleic acid molecules of the invention can be used to express a HDGFX protein (e.g., via a recombinant expression vector in a host cell in gene therapy applications), to detect a HDGFX mRNA (e.g., in a biological sample) or a genetic lesion in a HDGFX gene, and to modulate HDGFX activity, as described further below. In addition, the HDGFX proteins can be used to screen drugs or compounds that modulate the HDGFX activity or expression as well as to treat disorders characterized by insufficient or excessive production of the HDGFX protein, for example proliferative or differentiative disorders, or production of the HDGFX protein forms that have decreased or aberrant activity compared to the HDGFX wild type protein. In addition, the anti-HDGFX antibodies of the invention can be used to detect and isolate HDGFX proteins and modulate HDGFX activity.

This invention further pertains to novel agents identified by the above described screening assays and uses thereof for treatments as described herein.

Screening Assays

The invention provides methods (also referred to herein as "screening assays") for identifying modulators, i.e., candidate or test compounds or agents (e.g., proteins, polypeptides, nucleic acids or polynucleotides, peptides, peptidomimetics, small molecules including agonists or antagonists, or other drugs) that bind to HDGFX proteins or have a stimulatory or inhibitory effect on, for example, HDGFX expression or HDGFX activity. The candidate or test compounds or agents that may bind to a HDGFX polypeptide may have a molecular weight around 50 Da, 100 Da, 150 Da, 300 Da, 330 Da, 350 Da, 400 Da, 500 Da, 750 Da, 1000 Da, 1250 Da, 1500 Da, 1750 Da, 2000 Da, 5000 Da, 10,000 Da, 25,000 Da, 50,000 Da, 75,000 Da, 100,000 Da or more than 100,000 Da. In certain embodiments, the candidate substance that binds to a HDGFX polypeptide has a molecular weight not more than about 1500 Da.

Details of functional assays are provided herein further below. Any of the assays described, as well as additional assays known to practitioners in the fields of pharmacology, hematology, internal medicine, oncology and the like, may be employed in order to screen candidate substance for their properties as therapeutic agents. As noted, the therapeutic agents of the invention encompass proteins, polypeptides, nucleic acids or polynucleotides, peptides, peptidomimetics, small molecules including agonists or antagonists, or other drugs described herein.

In one embodiment, the invention provides assays for screening candidate or test compounds which bind to or modulate the activity of a HDGFX protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) *Anticancer Drug Des* 12:145).

Examples of methods for the synthesis of molecular libraries can be found in the art, for example in: DeWitt et al. (1993) *Proc Natl Acad Sci U.S.A.* 90:6909; Erb et al. (1994) *Proc Natl Acad Sci U.S.A.* 91:11422; Zuckermann et al. (1994) *J Med Chem* 37:2678; Cho et al. (1993) *Science* 261:1303; Carrell et al. (1994) *Angew Chem Int Ed Engl* 33:2059; Carell et al. (1994) *Angew Chem Int Ed Engl* 33:2061; and Gallop et al. (1994) *J Med Chem* 37:1233.

Libraries of compounds may be presented in solution (e.g., Houghten (1992) *Biotechniques* 13:412–421), or on beads (Lam (1991) *Nature* 354:82–84), on chips (Fodor (1993) *Nature* 364:555–556), bacteria (Ladner U.S. Pat. No. 5,223,409), spores (Ladner U.S. Pat. No. 5,223,409), plasmids (Cull et al. (1992) *Proc Natl Acad Sci USA* 89:1865–1869) or on phage (Scott and Smith (1990) *Science* 249:386–390; Devlin (1990) *Science* 249:404–406; Cwirla et al. (1990) *Proc Natl Acad Sci U.S.A.* 87:6378–6382; Felici (1991) *J Mol Biol* 222:301–310; Ladner above.).

In one embodiment, an assay is a cell-based assay in which a cell which expresses a membrane-bound form of a HDGFX protein, or a biologically active portion thereof, on the cell surface is contacted with a test compound and the ability of the test compound to bind to a HDGFX protein determined. The cell, for example, can of mammalian origin or a yeast cell. Determining the ability of the test compound to bind to the HDGFX protein can be accomplished, for example, by coupling the test compound with a radioisotope or enzymatic label such that binding of the test compound to the HDGFX protein or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In one embodiment, the assay comprises contacting a cell which expresses a membrane-bound form of a HDGFX protein, or a biologically active portion thereof, on the cell surface with a known compound which binds a HDGFX to form an assay mixture, contacting the assay mixture with a test compound, and determining the ability of the test compound to interact with a HDGFX protein, wherein determining the ability of the test compound to interact with a HDGFX protein comprises determining the ability of the test compound to preferentially bind to a HDGFX or a biologically active portion thereof as compared to the known compound.

In another embodiment, an assay is a cell-based assay comprising contacting a cell expressing a membrane-bound form of a HDGFX protein, or a biologically active portion thereof, on the cell surface with a test compound and determining the ability of the test compound to modulate (e.g., stimulate or inhibit) the activity of the HDGFX protein or biologically active portion thereof. Determining the ability of the test compound to modulate the activity of a HDGFX polypeptide or a biologically active portion thereof can be accomplished, for example, by determining the ability of the HDGFX protein to bind to or interact with a HDGFX target molecule. As used herein, a "target molecule" is a molecule with which a HDGFX protein binds or interacts in nature, for example, a molecule on the surface of a cell which expresses a HDGFX interacting protein, a molecule on the surface of a second cell, a molecule in the extracellular milieu, a molecule associated with the internal surface of a cell membrane or a cytoplasmic molecule. A HDGFX target molecule can be a non-HDGFX molecule or a HDGFX protein or polypeptide of the present invention. In one embodiment, a HDGFX target molecule is a component of a signal transduction pathway that facilitates transduction of an extracellular signal (e.g., a signal generated by binding of a compound to a membrane-bound HDGFX molecule) through the cell membrane and into the cell. The target, for example, can be a second intercellular protein that has catalytic activity or a protein that facilitates the association of downstream signaling molecules with the HDGFX polypeptide.

Determining the ability of the HI)GFX protein to bind to or interact with a HDGFX target molecule can be accomplished by one of the methods described above for determining direct binding. In one embodiment, determining the ability of the HDGFX protein to bind to or interact with a HDGFX target molecule can be accomplished by determining the activity of the target molecule. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising a HDGFX-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the present invention is a cell-free assay comprising contacting a HDGFX protein or biologically active portion thereof with a test compound and determining the ability of the test compound to bind to the HDGFX protein or biologically active portion thereof. Binding of the test compound to the HDGFX protein can be determined either directly or indirectly as described above. In one embodiment, the assay comprises contacting the HDGFX protein or biologically active portion thereof with a known compound which binds HDGFX to form an assay mixture, contacting the assay mixture with a test compound, and determining the ability of the test compound to interact with a HDGFX protein, wherein determining the ability of the test compound to interact with a HDGFX protein comprises determining the ability of the test compound to preferentially bind to a HDGFX or biologically active portion thereof as compared to the known compound.

In another embodiment, an assay is a cell-free assay comprising contacting a HDGFX protein or biologically active portion thereof with a test compound and determining the ability of the test compound to modulate (e.g., stimulate or inhibit) the activity of the HDGFX protein or biologically active portion thereof. Determining the ability of the test compound to modulate the activity of a HDGFX polypeptide can be accomplished, for example, by determining the ability of the HDGFX protein to bind to a HDGFX target molecule by one of the methods described above for determining direct binding. In an alternative embodiment, determining the ability of the test compound to modulate the activity of a HDGFX polypeptide can be accomplished by determining the ability of the HDGFX protein further modulate a HDGFX target molecule. For example, the catalytic/enzymatic activity of the target molecule on an appropriate substrate can, be determined as previously described.

In yet another embodiment, the cell-free assay comprises contacting the HDGFX protein or biologically active portion thereof with a known compound which binds a HDGFX polypeptide to form an assay mixture, contacting the assay mixture with a test compound, and determining the ability of the test compound to interact with a HDGFX protein, wherein determining the ability of the test compound to interact with a HDGFX protein comprises determining the ability of the HDGFX protein to preferentially bind to or modulate the activity of a HDGFX target molecule.

The cell-free assays of the present invention are amenable to use of both a soluble form or a membrane-bound form of a HDGFX polypeptide. In the case of cell-free assays comprising the membrane-bound form of a HDGFX polypeptide, it may be desirable to utilize a solubilizing agent such that the membrane-bound form of a HDGFX polypeptide is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, N-dodecyl-N,N-dimethyl-3-ammonio-1-propane sulfonate, 3-(3-cholamidopropyl)dimethylaminiol-propane sulfonate (CHAPS), or 3-(3-cholamidopropyl)dimethylamminiol-2-hydroxy-1-propane sulfonate (CHAPSO).

It may be desirable to immobilize either a HDGFX polypeptide or its target molecule to facilitate separation of complexed from uncomplexed forms of one or both of the proteins, as well as to accommodate automation of the assay. Binding of a test compound to a HDGFX polypeptide, or interaction of a HDGFX polypeptide with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, GST-HDGFX polypeptide fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or a HDGFX protein, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of a HDGFX binding or activity determined using standard techniques.

Other techniques for immobilizing proteins on matrices can also be used in the screening assays of the invention. For example, either the HDGFX polypeptide or its target molecule can be immobilized utilizing conjugation of biotin and streptavidin. Biotinylated HDGFX protein or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with HDGFX protein or target molecules, but which do not interfere with binding of the HDGFX protein to its target molecule, can be derivatized to the wells of the plate, and unbound target or HDGFX protein trapped in the wells by antibody conjugation. Methods for detecting such complexes, in addition to those described above for the GST-immobilized complexes, include immunodetection of complexes using antibodies reactive with the HDGFX protein or target molecule, as well as enzyme-linked assays that rely on detecting an enzymatic activity associated with the HDGFX protein or target molecule.

In another embodiment, modulators of a HDGFX expression are identified in a method wherein a cell is contacted with a candidate compound and the expression of a HDGFX mRNA or protein in the cell is determined. The level of expression of a HDGFX mRNA or protein in the presence of the candidate compound is compared to the level of expression of a HDGFX mRNA or protein in the absence of the candidate compound. The candidate compound can then be identified as a modulator of a HDGFX expression based on this comparison. For example, when expression of a HDGFX mRNA or protein is greater (statistically significantly.greater) in the presence of the candidate compound than in its absence, the candidate compound is identified as a stimulator of a HDGFX mRNA or protein expression. Alternatively, when expression of a HDGFX mRNA or protein is less (statistically significantly less) in the presence of the candidate compound than in its absence, the candidate compound is identified as an inhibitor of a HDGFX mRNA or protein expression. The level of a HDGFX mRNA or protein expression in the cells can be determined by methods described herein for detecting HDGFX mRNA or protein.

In yet another aspect of the invention, the HDGFX proteins can be used as "bait proteins" in a two-hybrid assay or three hybrid assay (see, e.g., U.S. Pat. No. 5,283,317; Zervos et al. (1993) Cell 72:223–232; Madura et al. (1993) J Biol Chem 268:12046–12054; Bartel et al. (1993) Biotechniques 14:920–924; Iwabuchi et al. (1993) Oncogene 8:1693–1696; and Brent WO94/10300), to identify other proteins that bind to or interact with the HDGFX ("HDGFX-binding proteins" or "HDGFX-bp") and modulate HDGFX activity. Such HDGFX-binding proteins are also likely to be involved in the propagation of signals by the HDGFX proteins as, for example, upstream or downstream elements of the HDGFX pathway.

The two-hybrid system is based on the modular nature of most transcription factors, which consist of separable DNA-binding and activation domains. Briefly, the assay utilizes two different DNA constructs. In one construct, the gene that codes for a HDGFX is fused to a gene encoding the DNA binding domain of a known transcription.factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a HDGFX-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with the HDGFX.

Screening can also be performed in vivo. For example, in one embodiment, the invention includes a method for screening for a modulator of activity or of latency or predisposition to a HDGFX-associated disorder by administering a test compound or to a test animal at increased risk for a HDGFX-associated disorder. In some embodiments, the test animal recombinantly expresses a HDGFX polypeptide. Activity of the polypeptide in the test animal after administering the compound is measured, and the activity of the protein in the test animal is compared to the activity of the polypeptide in a control animal not administered said polypeptide. A change in the activity of said polypeptide in said test animal relative to the control animal indicates the test compound is a modulator of latency of or predisposition to a HDGFX-associated disorder.

In some embodiments, the test animal is a recombinant test animal that expresses a test protein transgene or expresses the transgene under the control of a promoter at an increased level relative to a wild-type test animal. Preferably, the promoter is not the native gene promoter of the transgene.

This invention further pertains to novel agents identified by the above-described screening assays and uses thereof for treatments as described herein.

Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample.

The HDGFX sequences of the present invention can also be used to identify individuals from minute biological samples. In this technique, an individual's genomic DNA is digested with one or more restriction enzymes, and probed on a Southern blot to yield unique bands for identification. The sequences of the present invention are useful as additional DNA markers for RFLP ("restriction fragment length polymorphisms," described in U.S. Pat. No. 5,272,057).

Furthermore, the sequences of the present invention can be used to provide an alternative technique that determines the actual base-by-base DNA sequence of selected portions of an individual's genome. Thus, the HDGFX sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The HDGFX sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Much of the allelic variation is due to single nucleotide polymorphisms (SNPs), which include restriction fragment length polymorphisms (RFLPs).

Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, as described above, can comfortably provide positive individual identification with a panel of perhaps 10 to 1,000 primers that each yield a noncoding amplified sequence of 100 bases. If predicted coding sequences are used, a more appropriate number of primers for positive individual identification would be 500–2,000.

Use of Partial HDGFX Sequences in Forensic Biology

DNA-based identification techniques based on HDGFX nucleic acid sequences or polypeptide sequences can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, that can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding regions, making it easier to differentiate individuals using this technique. Examples of polynucleotide reagents include the HDGFX sequences or portions thereof, e.g., fragments derived from the noncoding regions of of SEQ ID NO:1, having a length of at least 20 bases, preferably at least 30 bases.

The HDGFX sequences described herein can further be used to provide polynucleotide reagents, e.g., labeled or label-able probes that can be used, for example, in an in situ hybridization technique, to identify a specific tissue, e.g., brain tissue, etc. This can be very useful in cases where a forensic pathologist is presented with a tissue of unknown origin. Panels of such HDGFX probes can be used to identify tissue by species and/or by organ type.

In a similar fashion, these reagents, e.g., HDGFX primers or probes can be used to screen tissue culture for contamination (i.e. screen for the presence of a mixture of different types of cells in a culture).

Predictive Medicine

The present invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining a HDGFX protein and/or nucleic acid expression as well as HDGFX activity, in the context of a biological sample (e.g., blood, serum, cells, tissue) to thereby determine whether an individual is afflicted with a disease or disorder, or is at risk of developing a disorder, associated with aberrant HDGFX expression or activity. The invention also provides for prognostic (or predictive) assays for determining whether an individual is at risk of developing a disorder associated with a HDGFX protein, nucleic acid expression or activity. For example, mutations in a HDGFX gene can be assayed in a biological sample. Such assays can be used for prognostic or predictive purpose to thereby prophylactically treat an individual prior to the onset of a disorder characterized by or associated with HDGFX protein, nucleic acid expression or activity.

Another aspect of the invention provides methods for determining HDGFX protein, nucleic acid expression or HDGFX activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs, compounds) on the expression or activity of a HDGFX in clinical trials.

These and other agents are described in further detail in the following sections.

Diagnostic Assays

Other conditions in which proliferation of cells plays a role include tumors, restenosis, psoriasis, Dupuytren's contracture, diabetic complications, Kaposi's sarcoma and rheumatoid arthritis.

A HDGFX polypeptide may be used to identify an interacting polypeptide a sample or tissue. The method comprises contacting the sample or tissue with the HDGFX, allowing formation of a complex between the HDGFX polypeptide and the interacting polypeptide, and detecting the complex, if present.

The proteins of the invention may be used to stimulate production of antibodies specifically binding the proteins. Such antibodies may be used in immunodiagnostic procedures to detect the occurrence of the protein in a sample. The proteins of the invention may be used to stimulate cell growth and cell proliferation in conditions in which such growth would be favorable. An example would be to counteract toxic side effects of chemotherapeutic agents on, for example, hematopoiesis and platelet formation, linings of the gastrointestinal tract, and hair follicles. They may also be used to stimulate new cell growth in neurological disorders including, for example, Alzheimer's disease. Alternatively, antagonistic treatments may be administered in which an antibody specifically binding the HDGFX-like proteins of the invention would abrogate the specific growth-inducing effects of the proteins. Such antibodies may be useful, for example, in the treatment of proliferative disorders including various tumors and benign hyperplasias.

Polynucleotides or oligonucleotides corresponding to any one portion of the HDGFX nucleic acids of SEQ ID NO:1 may be used to detect DNA containing a corresponding ORF gene, or detect the expression of a corresponding HDGFX gene, or HDGFX-like gene. For example, a HDGFX nucleic acid expressed in a particular cell or tissue, as noted in Table 3, can be used to identify the presence of that particular cell type.

An exemplary method for detecting the presence or absence of a HDGFX polypeptide in a biological sample involves obtaining a biological sample from a test subject and contacting the biological sample with a compound or an agent capable of detecting a HDGFX protein or nucleic acid (e.g, mRNA, genomic DNA) that encodes a HDGFX protein such that the presence of a HDGFX polypeptide is detected in the biological sample. An agent for detecting a HDGFX mRNA or genomic DNA is a labeled nucleic acid probe capable of hybridizing to a HDGFX mRNA or genomic DNA. The nucleic acid probe can be, for example, a full-length HDGFX nucleic acid, such as the nucleic acid of SEQ ID NO:1, or a portion thereof, such as an oligonucleotide of at least 15, 30, 50, 100, 250 or 500 nucleotides in length and sufficient to specifically hybridize under stringent conditions to a HDGFX mRNA or genomic DNA, as described above. Other suitable probes for use in the diagnostic assays of the invention are described herein.

An agent for detecting a HDGFX protein is an antibody capable of binding to a HDGFX protein, preferably an antibody with a detectable label. Antibodies can be polyclonal, or more preferably, monoclonal. An intact antibody, or afragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect a HDGFX mRNA, protein, or genomic DNA in a biological sample in vitro as well as in vivo. For example, in vitro techniques for detection of a HDGFX mRNA include Northern hybridizations and in situ hybridizations. In vitro techniques for detection of a HDGFX protein include enzyme linked immunosorbent assays (ELISAs), Western blots, immunoprecipitations and immunofluorescence. In vitro techniques for detection of a HDGFX genomic DNA include Southern hybridizations. Furthermore, in vivo techniques for detection of a HDGFX protein include introducing into a subject a labeled anti-HDGFX antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting a HDGFX protein, mRNA, or genomic DNA, such that the presence of a HDGFX protein, mRNA or genomic DNA is detected in the biological sample, and comparing the presence of a HDGFX protein, mRNA or genomic DNA in the control sample with the presence of a HDGFX protein, mRNA or genomic DNA in the test sample.

The invention also encompasses kits for detecting the presence of a HDGFX polypeptide in a biological sample. For example, the kit can comprise: a labeled compound or agent capable of detecting a HDGFX protein or mRNA in a biological sample; means for determining the amount of a HDGFX polypeptide in the sample; and means for comparing the amount of a HDGFX polypeptide in the sample with a standard. The compound or agent can be packaged in a suitable container. The kit can further comprise instructions for using the kit to detect a HDGFX protein or nucleic acid.

Prognostic Assays

The diagnostic methods described herein can furthermore be utilized to identify subjects having or at risk of developing a disease or disorder associated with aberrant HDGFX polypeptide expression or activity. For example, the assays described herein, such as the preceding diagnostic assays or the following assays, can be utilized to identify a subject having or at risk of developing a disorder associated with a HDGFX protein, nucleic acid expression or activity in, e.g., proliferative or differentiative disorders such as hyperplasias, tumors, restenosis, psoriasis, Alzheimer's disease, etc. Alternatively, the prognostic assays can be utilized to identify a subject having or at risk for developing a disease or disorder. Thus, the present invention provides a method for identifying a disease or disorder associated with aberrant HDGFX expression or activity in which a test sample is obtained from a subject and a HDGFX protein or nucleic acid (e.g., mRNA, genomic DNA) is detected, wherein the presence of a HDGFX protein or nucleic acid is diagnostic for a subject having or at risk of developing a disease or disorder associated with aberrant HDGFX expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant HDGFX expression or activity. For example, such methods can be used to determine whether a subject can be effectively treated with an agent for a disorder, such as a proliferative disorder, differentiative disorder, glia-associated disorders, etc. Thus, the present invention provides methods for determining whether a subject can be effectively treated with an agent for a disorder associated with aberrant HDGFX expression or activity in which a test sample is obtained and a HDGFX protein or nucleic acid is detected (e.g., wherein the presence of a HDGFX protein or nucleic acid is diagnostic for a subject that can be administered the agent to treat a disorder associated with aberrant HDGFX expression or activity.)

The methods of the invention can also be used to detect genetic lesions in a HDGFX gene, thereby determining if a subject with the lesioned gene is at risk for, or suffers from, a proliferative disorder, differentiative disorder, glia-associated disorder, etc. In various embodiments, the methods include detecting, in a sample of cells from the subject, the presence or absence of a genetic lesion characterized by at least one of an alteration affecting the integrity of a gene encoding a HDGFX protein, or the mis-expression of the HDGFX gene. For example, such genetic lesions can be detected by ascertaining the existence of at least one of (1) a deletion of one or more nucleotides from a HDGFX gene; (2) an addition of one or more nucleotides to a HDGFX gene; (3) a substitution of one or more nucleotides of a HDGFX gene, (4) a chromosomal rearrangement of a HDGFX gene; (5) an alteration in the level of a messenger RNA transcript of a HDGFX gene, (6) aberrant modification of a HDGFX gene, such as of the methylation pattern of the genomic DNA, (7) the presence of a non-wild type splicing pattern of a messenger RNA transcript of a HDGFX gene, (8) a non-wild type level of a protein, (9) allelic loss of a HDGFX gene, and (10) inappropriate post-translational modification of a HDGFX protein. As described herein, there are a large number of assay techniques known in the art which can be used for detecting lesions in a HDGFX gene. A preferred biological sample is a peripheral blood leukocyte sample isolated by conventional means from a subject. However, any biological sample containing nucleated cells may be used, including, for example, buccal mucosal cells.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR or, alternatively, in a ligation chain reaction (LCR) (see, e.g., Landegran et al. (1988) *Science* 241:1077–1080; and Nakazawa et al. (1 994) *PNAS* 91:360–364), the latter of which can be particularly useful for detecting point mutations in the HDGFX gene (see Abravaya et al. (1995) *Nucl Acids Res* 23:675–682). This method can include the steps of collecting a sample of cells from a patient, isolating nucleic acid (e.g., genomic, mRNA or both) from the cells of the sample, contacting the nucleic acid sample with one or more primers that specifically hybridize to a HDGFX gene under conditions such that hybridization and amplification of the HDGFX gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al., 1990, *Proc Natl Acad Sci USA* 87:1874–1878), transcriptional amplification system (Kwoh, et al., 1989, *Proc Natl Acad Sci USA* 86:1173–1177), Q-Beta Replicase (Lizardi et al, 1988, *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a HDGFX gene from a sample cell can be identified by alterations in restriction enzyme cleavage patterns. For example, sample and control DNA is isolated, amplified (optionally), digested with one or more restriction endonucleases, and fragment length sizes are determnined by gel electrophoresis and compared. Differences in fragment length sizes between sample and control DNA indicates mutations in the sample DNA. Moreover, the use of sequence specific ribozymes (see, for example, U.S. Pat. No. 5,493,531) can be used to score for the presence of specific mutations by development or loss of a ribozyme cleavage site.

In other embodiments, genetic mutations in a HDGFX nucleic acid of the invention can be identified by hybridizing a sample and control nucleic acids, e.g., DNA or RNA, to high density arrays containing hundreds or thousands of oligonucleotides probes (Cronin et al. (1996) *Human Mutation* 7: 244–255; Kozal et al. (1996) *Nature Medicine* 2: 753–759). For example, genetic mutations in a HDGFX of the invention can be identified in two dimensional arrays containing light-generated DNA probes as described in Cronin et al. above. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the HDGFX gene and detect mutations by comparing the sequence of the sample HDGFX gene with the corresponding wild-type (control) sequence. Examples of sequencing reactions include those based on techniques developed by Maxim and Gilbert (1977) *PNAS* 74:560 or Sanger (1977) *PNAS* 74:5463. It is also contemplated that any of a variety of automated sequencing procedures can be utilized when performing the diagnostic assays (Naeve et al., (1995) *Biotechniques* 19:448), including sequencing by mass spectrometry (see, e.g, PCT International Publ. No. WO 94/16101; Cohen et al. (1996) *Adv Chromatogr* 36:127–162; and Griffin et al. (1993) *Appl Biochem Biotechnol* 38:147–159).

Other methods for detecting mutations in the HDGFX gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type HDGFX sequence with potentially mutant RNA or DNA obtained from a tissue sample. The double-stranded duplexes are treated with an agent that cleaves singlestranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either RNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *Proc Natl Acad Sci USA* 85:4397; Saleeba et al (1992) *Methods Enzymol* 217:286–295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in HDGFX cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a HDGFX sequence, e.g., a wild-type HDGFX sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in HDGFX genes. For example, single strand conformation polymorphism (SSCP) may be used to detect differences in electrophoretic mobility between mutant and wild type nucleic acids (Orita et al. (1989) *Proc Natl Acad Sci USA*: 86:2766, see also Cotton (1993) *Mutat Res* 285:125–144; Hayashi (1992) *Genet Anal Tech Appl* 9:73–79). Single-stranded DNA fragments of sample and control a HDGFX nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA, rather than DNA, in which the secondary structure is more sensitive to a change in sequence. In one embodiment, the subject method utilizes heteroduplex analysis to separate double stranded heteroduplex molecules on the basis of changes in electrophoretic mobility. See, e.g., Keen et al. (1991) *Trends Genet* 7:5.

In yet another embodiment the movement of mutant or wild-type fragments in polyacrylamide gels containing a gradient of denaturant is assayed using denaturing gradient gel electrophoresis (DGGE). See, e.g., Myers et al (1985) *Nature* 313:495. When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA. See, e.g., Rosenbaum and Reissner (1 987) *Biophys Chem* 265:12753.

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found. See, e.g., Saiki et al. (1986) *Nature* 324:163); Saiki et al. (1989) *Proc Natl Acad. Sci USA* 86:6230. Such allele specific oligonucleotides are hybridized to PCR amplified target DNA or a number of different mutations when the oligonucleotides are attached to the hybridizing membrane and hybridized with labeled target DNA.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection. See, e.g., Gasparini et al (1992) *Mol Cell Probes* 6:1. It is anticipated that in certain embodiments amplification may also be performed using Taq ligase for amplification. See, e.g., Barany (1991) *Proc Natl Acad Sci USA* 88:189. In such cases, ligation will occur only if there is a perfect match at the 3' end of the 5' sequence, making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a HDGFX gene.

Furthermore, any cell type or tissue, preferably peripheral blood leukocytes, in which a HDGFX of the invention is expressed may be utilized in the prognostic assays described herein. However, any biological sample containing nucleated cells may be used, including, for example, buccal mucosal cells.

Pharmacogenomics

Agents, or modulators that have a stimulatory or inhibitory effect on HDGFX activity (e.g., HDGFX gene expression), as identified by a screening assay described herein can be administered to individuals to treat (prophylactically or therapeutically) disorders (e.g., neurological, cancer-related or gestational disorders) associated with aberrant HDGFX activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of a HDGFX protein, expression of a HDGFX nucleic acid, or mutation content of a HDGFX genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See e.g., Eichelbaum, 1996, *Clin Exp Pharmacol Physiol*, 23:983–985 and Linder, 1997, *Clin Chem*, 43:254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase (G6PD) deficiency is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of a HDGFX protein, expression of a HDGFX nucleic acid, or mutation content of a HDGFX genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a HDGFX modulator, such as a modulator identified by one of the exemplary screening assays described herein.

Monitoring Clinical Efficacy

Monitoring the influence of agents (e.g., drugs, compounds) on the expression or activity of a HDGFX (e.g., the ability to modulate aberrant cell proliferation and/or differentiation) can be applied in basic drug screening and in clinical trials. For example, the effectiveness of an agent determined by a screening assay as described herein to increase HDGFX gene expression, protein levels, or upregulate HDGFX activity, can be monitored in clinical trials of subjects exhibiting decreased HDGFX gene expression, protein levels, or downregulated HDGFX activity. Alternatively, the effectiveness of an agent determined by a screening assay to decrease HDGFX gene expression, protein levels, or downregulate HDGFX activity, can be monitored in clinical trials of subjects exhibiting increased HDGFX gene expression, protein levels, or upregulated HDGFX activity. In such clinical trials, the expression or activity of a HDGFX and, preferably, other genes that have been implicated in, for example, a proliferative or neurological disorder, can be used as a "read out" or marker of the responsiveness of a particular cell. Other HDGFX-associated disorders include, e.g., cancers, cell proliferation disorders, neurological disorders; and fertility disorders.

For example, genes, including genes encoding a HDGFX of the invention, that are modulated in cells by treatment with an agent (e.g., compound, drug or small molecule) that modulates a HDGFX activity (e.g., identified in a screening assay as described herein) can be identified. Thus, to study the effect of agents on cellular proliferation disorders, for example, in a clinical trial, cells can be isolated and RNA prepared and analyzed for the levels of expression of a HDGFX and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of a gene or other genes. In this way, the gene expression pattern can serve as a marker, indicative of the physiological response of the cells to the agent. Accordingly, this response state may be determined before, and at various points during, treatment of the individual with the agent.

In one embodiment, the invention provides a method for monitoring the effectiveness of treatment of a subject with an agent (e.g., an agonist, antagonist, protein, peptide, nucleic acid, peptidomimetic, small molecule, or other drug candidate identified by the screening assays described herein) comprising the steps of (i) obtaining a pre-administration sample from a subject prior to administration of the agent; (ii) detecting the level of expression of a HDGFX protein, mRNA, or genomic DNA in the preadministration sample; (iii) obtaining one or more post-administration samples from the subject; (iv) detecting the level of expression or activity of the HDGFX protein, mRNA, or genomic DNA in the post-administration samples; (v) comparing the level of expression or activity of the HDGFX protein, mRNA, or genomic DNA in the pre-administration sample with the HDGFX protein, mRNA, or genomic DNA in the post administration sample or samples; and (vi) altering the administration of the agent to the subject accordingly. For example, increased administration of the agent may be desirable to increase the expression or activity of a HDGFX to higher levels than detected, i.e., to increase the effectiveness of the agent. Alternatively, decreased administration of the agent may be desirable to decrease expression or activity of a HDGFX to lower levels than detected, i.e., to decrease the effectiveness of the agent.

Methods of Treatment

The present invention provides for both prophylactic and therapeutic methods of treating a subject at risk of (or susceptible to) a disorder or having a disorder associated with aberrant HDGFX expression or activity.

Diseases and disorders that are characterized by increased (relative to a subject not suffering from the disease or disorder) levels or biological activity may be treated with Therapeutics that antagonize (i.e., reduce or inhibit) activity. Therapeutics that antagonize activity may be administered in a therapeutic or prophylactic manner. Therapeutics that may be utilized include, but are not limited to, (i) a HDGFX polypeptide, or analogs, derivatives, fragments or homologs thereof; (ii) antibodies to a HDGFX peptide; (iii) nucleic acids encoding a HDGFX peptide; (iv) administration of antisense nucleic acid and nucleic acids that are "dysfunctional" (i.e., due to a heterologous insertion within the coding sequences of coding sequences to a HDGFX polypeptide) that are utilized to "knockout" endogenous function of a HDGFX polypeptide by homologous recombination (see, e.g., Capecchi, 1989, Science 244: 1288–1292); or (v) modulators (i.e., inhibitors, agonists and antagonists, including additional peptide mimetic of the invention or antibodies specific to a peptide of the invention) that alter the interaction between a HDGFX peptide and its binding partner.

Diseases and disorders that are characterized by decreased (relative to a subject not suffering from the disease or disorder) levels or biological activity may be treated with Therapeutics that increase (i.e., are agonists to) activity. Therapeutics that upregulate activity may be administered in a therapeutic or prophylactic manner. Therapeutics that may be utilized include, but are not limited to, a polypeptide, a peptide, or analogs, derivatives, fragments or homologs thereof; or an agonist that increases bioavailability.

Increased or decreased levels can be readily detected by quantifying peptide and/or RNA, by obtaining a patient tissue sample (e.g., from biopsy tissue) and assaying it in vitro for RNA or polypeptide levels, structure and/or activity of the expressed polypeptides (or mRNAs encoding a HDGFX polypeptide). Methods that are well-known within the art include, but are not limited to, immunoassays (e.g., by Western blot analysis, imniunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, etc.).

In one aspect, the invention provides a method for preventing, in a subject, a disease or condition associated with aberrant HDGFX expression or activity, by administering to the subject an agent that modulates HDGFX expression or at least one HDGFX activity. Subjects at risk for a disease that is caused or contributed to by aberrant HDGFX expression or activity can be identified by, for example, any or a combination of diagnostic or prognostic assays as described herein. Administration of a prophylactic agent can occur prior to the manifestation of symptoms characteristic of the HDGFX aberrancy, such that a disease or disorder is prevented or, alternatively, delayed in its progression. Depending on the type of a HDGFX aberrancy, for example, a HDGFX agonist or HDGFX antagonist agent can be used for treating the subject. The appropriate agent can be determined based on screening assays described herein.

Another aspect of the invention pertains to methods of modulating HDGFX expression or activity for therapeutic purposes. The modulatory method of the invention involves contacting a cell with an agent that modulates one or more of the activities of a HDGFX protein activity associated with the cell. An agent that modulates a HDGFX protein activity can be an agent as described herein, such as a nucleic acid or a protein, a naturally-occurring cognate ligand of a HDGFX protein, a peptide, a HDGFX peptidomimetic, or other small molecule. In one embodiment, the agent stimulates one or more a HDGFX protein activity. Examples of such stimulatory agents include active a HDGFX protein and a nucleic acid molecule encoding a HDGFX polypeptide that has been introduced into the cell. In another embodiment, the agent inhibits one or more a HDGFX protein activity. Examples of such inhibitory agents include antisense a HDGFX nucleic acid molecules and anti-HDGFX antibodies. These modulatory methods can be performed in vitro (e.g., by culturing the cell with the agent)

or, alternatively, in vivo (e.g., by administering the agent to a subject). As such, the present invention provides methods of treating an individual afflicted with a disease or disorder characterized by aberrant expression or activity of a HDGFX protein or nucleic acid molecule. In one embodiment, the method involves administering an agent (e.g., an agent identified by a screening assay described herein), or combination of agents that modulates (e.g., upregulates or downregulates) HDGFX expression or activity. In another embodiment, the method involves administering a HDGFX protein or nucleic acid molecule as therapy to compensate for reduced or aberrant HDGFX expression or activity.

The invention will be further illustrated in the following examples, which do not limit the scope of the claims.

EXAMPLES

Example 1

Molecular Cloning of HDGFX

The predicted open reading frame codes for a 251 amino acid long protein with an overall 59% identity, on the amino acid level, to the bovine hepatoma derived growth factor related protein 3 (HRP-3) (TREMBLNEW-ACC:CAB40348). The predicted full length ORF has been cloned and verified.

Cloning the Full Length HDGFX

Oligonucleotide primers were designed to PCR amplify a DNA segment coding for the full length HDGFX gene product. The forward primer includes an in-frame BamHI restriction site and a consensus Kozak sequence. The reverse primer contains an in-frame XhoI restriction site. The sequences of the PCR primers are the following:

HDGFX Forw: GGATCCACCATGTCGGCCTACG-GCATGCCCATGTAC (SEQ ID NO:11), and

HDGFX Rev: CTCGAGCAGGCTGTCGCGATCTC-CGCCGCC (SEQ ID NO:12).

PCR reactions were set up using a total of 5 ng mixture of cDNA template containing equal amounts of cDNAs derived from human fetal brain, human testis, human mammary and human skeletal muscle tissues, 1 microM of each of the HDGFX Forw and HDGFX Rev primers, 5 micromoles dNTP (Clontech Laboratories, Palo Alto Calif.) and 1 microliter of 50×Advantage-HF 2 polymerase (Clontech Laboratories, Palo Alto Calif.) in a 50 microliter volume. The following PCR reaction conditions were used:

a) 96° C. 3 minutes
b) 96° C. 30 seconds denaturation
c) 70° C. 30 seconds, primer annealing. This temperature was gradually decreased by 1° C./cycle
d) 72° C. 1 minute extension.
Repeat steps (b)–(d) 10 times
e) 96° C. 30 seconds denaturation
f) 60° C. 30 seconds annealing
g) 72° C. 1 minute extension
Repeat steps (e)–(g) 25 times
h) 72° C. 10 minutes final extension A PCR product having an approximate size of 750 bp was isolated after electrophoresis in agarose gel and ligated to the pCR2.1 vector (Invitrogen, Carlsbad, Calif.). The cloned insert was sequenced using vector specific M 13 Forward (−40) and M13. Reverse primers, as well as the following gene specific primers:

HDGFX S1: GACAAGCCGACCCACGCTGG (SEQ ID NO:13) and

HDGFX S2: CCAGCGTGGGTCGGCTTGTC (SEQ ID NO:14).

The sequence was verified as an open reading frame coding for the predicted HDGFX full length protein. The cloned sequence is 100% identical to the predicted translation product of SEQ ID NO:1. Theclone is called pCR2.1-AL033539-S321-4C.

Example 2

Construction of the Mammalian Expression Vector pCEP4/V5His

The oligonucleotide primers, pSec-V5-His Forward: CTCGTCCTCGAGGGTAAGC-CTATCCCTAAC (SEQ ID NO:15) and pSec-V5-His Reverse: CTCGTCGGGCCCCTGAT-CAGCGGGTTTAAAC (SEQ ID NO:16)

were designed to amplify a fragment from the expression vector pcDNA3.1-V5His (Invitrogen, Carlsbad, Calif.). The PCR product was digested with XhoI and ApaI and ligated into the XhoI/ApaI digested pSecTag2B vector (Invitrogen, Carlsbad Calif.). The correct structure of the resulting vector, pSecV5His, was verified by DNA sequence analysis. The vector pSecV5His was digested with PmeI and NheI, and the PmeI-NheI fragment was ligated into the BamHI/Klenow and NheI treated vector pCEP4 (Invitrogen, Carlsbad, Calif.). The resulting vector was named pCEP4/Sec. Subsequently, a KpnI and XhoI fragment from pcDNA3. IA (Invitrogen, Carlsbad, Calif.) was isolated and ligated into pCEP4/Sec that had been treated KpnI and XhoI. The resulting vector, named pCEP4/V5His lacks the IgKappa secretion signal originally present in pSecTag2B.

Example 3

Expression of HDGFX in Human Embryonic Kidney 293 Cells

A 0.8 kb BamHI-XhoI fragment containing the HDGFX sequence was isolated from pCR2.1-AL033539-S321–4C (Example 1) and subcloned into BamHI-XhoI digested pCEP4/V5His (Example 2) to generate expression vector pCEP4NV5His-AL033539. The pCEP4/V5His-AL033539 vector was transfected into 293 cells using the LipofectaminePlus reagent following the manufacturer's instructions (Gibco/BRL, Rockville, Md.). The cell pellet and supernatant were harvested 72 hours after transfection and examined for HDGFX expression by Western blotting run under reducing conditions with an anti-V5 antibody. FIG. 1 shows that the expressed HDGFX polypeptide has a molecular weight of approximately 50 kDa, which is secreted by 293 cells, as indicated by using SeeBlue molecular weight markers (Invitrogen, Carlsbad, Calif.).

Example 4

Construction of Recombinant E. coli Expression Vector pET(C)

The vector pBADgIII (Invitrogen Inc., Carlsbad, Calif.) was digested with NcoI and PmeI restriction enzymes to release a fragment of 150 bp containing BglII and SalI cloning sites and C-terminal 6×His tag. The plasmid pET28a (Novagen, Madison, Wis.) was linearized by digestion with the restriction enzyme XhoI and filled in with the Klenow fragment of the E. coli DNA polymerase. It was then digested with the restriction enzyme NcoI. Subsequently, the NcoI-PmeI fragment from pBADgIII was ligated into the linearized pET28a and the resulting E. coli expression vector was named as pET(C).

Example 5

Expression of HDGFX in Recombinant E. coli Using the Expression Vector pET(C)

Figure 2:
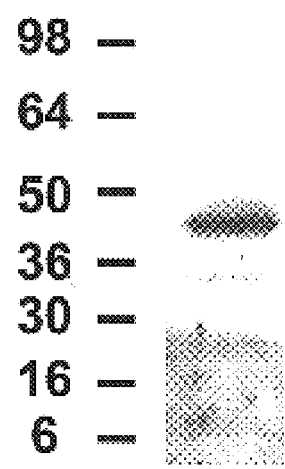
FIG. 2. Western blot of HDGFX polypeptide expressed in *E. coli* cells.

The BamHI-XhoI fragment containing the HDGFX gene (Examples 1 and 3) was ligated into the pET(C) vector (Example 4) that had been digested with BamHI and XhoI restriction enzymes. The resulting expression vector is named pET(C)-AL033539. In this vector, HDGFX was fused to the 6xHis tag at its C-terminus. The plasmid pET(C)-AL033539 was then transformed into the E. coli expression host BL21(DE3, pLys) (Novagen, Madison, Wis.). Expression of the HDGFX polypeptide was induced according to the manufacturer's instructions. After induction, total cells were harvested, and proteins were analyzed by Western blotting using anti-His antibody (Invitrogen, Carlsbad, Calif.). FIG. 2 shows that a HDGFX polypeptide was expressed as a polypeptide whose molecular weight is approximately 45 kDa in E. coli cells, as indicated by using SeeBlue molecular weight markers (Invitrogen, Carlsbad, Calif.).

Example 6

Cytokine Production in Monocytes in Response to Treatment with HDGFX.

Monocytes were isolated from fresh human peripheral blood mononuclear cells using CD14 microbeads (Miltenyi Biotec) according to the manufacture's procedure. Monocytes were plated in a 96-well flat bottom tissue culture treated plate at $1 \times 10^5$ cells per well in a volume of 100 µl per well in DMEM medium (Gibco, Rockville Md.) containing 10% fetal bovine serum (HyClone) and supplemented with L-glutamine, sodium pyruvate, non-essential amino acids, HEPES, and β-mercaptoethanol (supplements from Gibco/BRL, Rockville, Md.). HDGFX was purified from the secreted protein in the conditioned medium described in Example 3. HDGFX or vehicle control (20 mM Tris-HCl pH 7.4; 50 mM NaCl) was added to the wells and then the samples were incubated at 37° C. in a tissue culture incubator with 10% $CO_2$ for 24 hr. Tumor necrosis factor alpha (TNF α) or interleukin-6 (IL-6) production was measured by assaying the cell supernatant by ELISA (Pharmingen).

Figure 3:
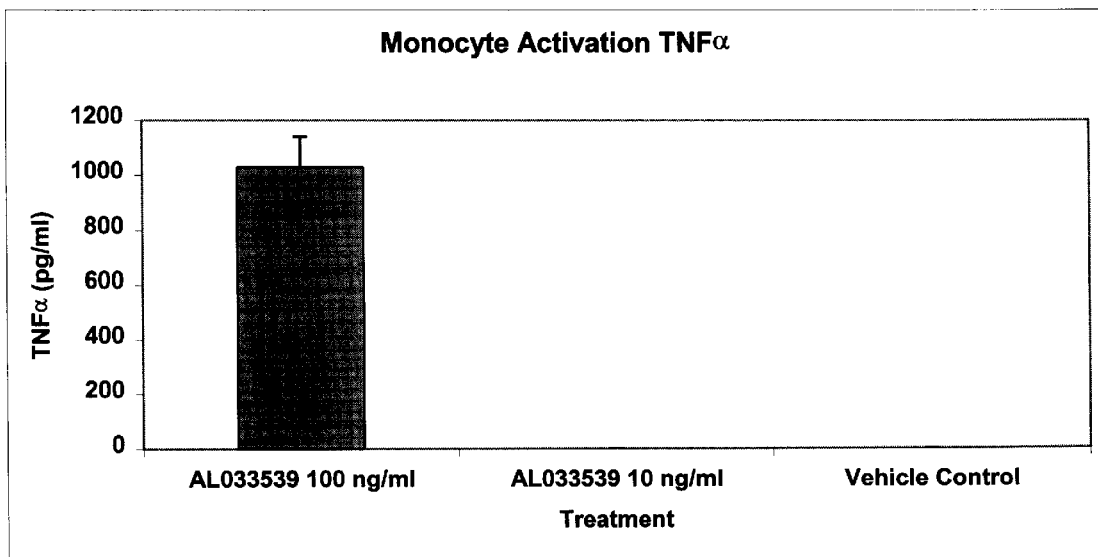
FIG. 3. Activation of monocytes in response to treatment with HDGFX as measured by secretion of tumor necrosis factor alpha.
Figure 4:
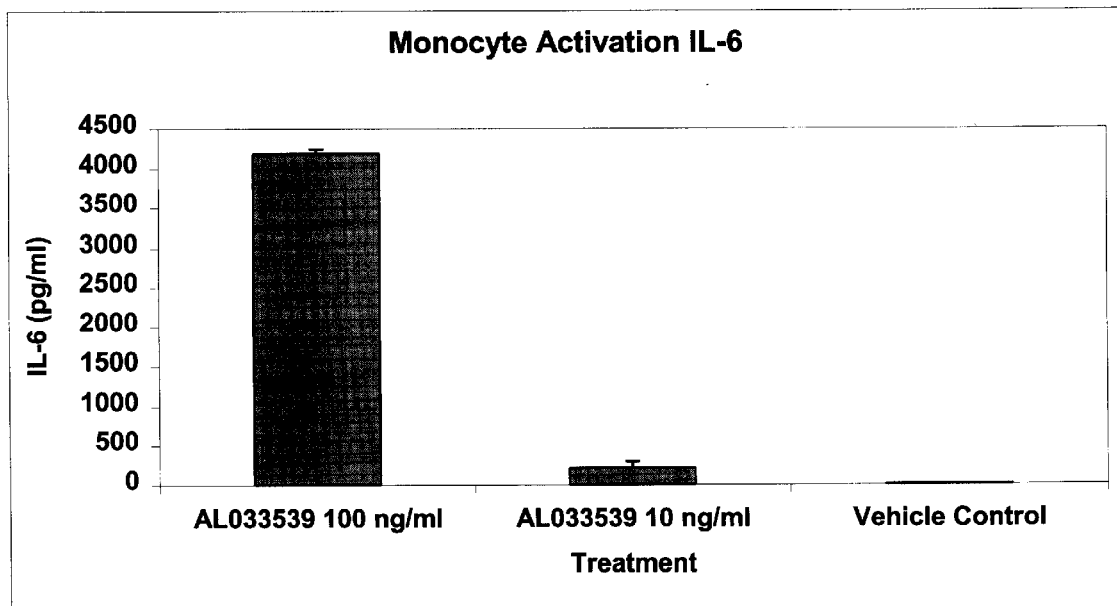
FIG. 4. Activation of monocytes in response to treatment with HDGFX as measured by secretion of interleukin-6.

The results are shown in FIGS. 3 and 4. Monocytes treated with 100 ng/ml HDGFX produced 23.8 ng/ml, IL-6 and 0.66 ng/ml TNF α. Monocytes treated with 10 ng/ml HDGFX produced 8.3 ng/ml IL-6, while TNF α production was not detected with treatment of 10 ng/ml HDGFX. Monocytes treated with the vehicle control did not produce detectable levels of IL-6 or TNF α. These results are representative of those obtained in a second, separate, experiment.

Example 7

In vivo Effects of Administration of HDGFX in Mice

HDGFX was purified from the secreted protein in the conditioned medium described in Example 3. Normal female BALB/c mice from-Harlan Labs were given single daily ip injections of HDGFX (5 mg/kg) or control vehicle (10 ml/kg) for 7 days. On the eighth day, animals were injected with HDGFX (5 mg/kg) and BrdU (100 mg/kg) and 1 hr later were anesthetized with Isoflurane and bled for determination of complete blood count (CBC) and clinical chemistry alterations. Tissues and organs were removed and weighed and collected into formalin for histopathologic evaluation which included BrdU immunohistochemistry for detection of proliferative changes. The results are shown in Table 5.

Relative spleen weights were increased 68% in mice treated with HDGFX compared to mice treated with vehicle control (0.683±0.044 grams (gr)/100 gr body wt vs. 0.407±0.08 gr/100 gr body wt). Also, relative liver weights were increased 11% in mice treated with HDGFX compared to mice treated with vehicle control (4.73±0.96 gr/100 gr body wt vs. 4.279±0.117 gr/100 gr body wt). Mice treated with HDGFX showed marked increase in granulocytopoiesis in the bone marrow compared to mice treated with vehicle control (myeloid:erythroid ratio 3:1 vs. 1:1). Treatment with HDGFX resulted in marked increases in splenic extramedullary hematopoiesis and lymphoid hyperplasia. Histopathology showed subacute inflammation affecting the pancreatic ducts with neutrophil and mononuclear cell infiltration and BrdU labeling was evident in the parenchyma in mice treated with HDGFX.

TABLE 5

| Animals # | BP # | 3/1/00 Body WT grams | 3/3/00 Body WT | 3/5/00 Body WT | 3/8/00 Final WT grams | Liver Weight grams | Rel. Liv. Wt. gr/100 gr | Spleen Weight grams | Rel. Spl. Wt. gr/100 gr | Comments/ Gross observations |
|---|---|---|---|---|---|---|---|---|---|---|
| Vehicle (Tris/PBS 10 ml/kg) | | | | | | | | | | |
| 1 | 548 | 19.03 | 19.4 | 19.3 | 19.5 | 0.81 | 4.154 | 0.077 | 0.395 | * |
| 2 | 549 | 19.02 | 19.5 | 19.3 | 19.8 | 0.864 | 4.364 | 0.086 | 0.434 | NSL |
| 3 | 550 | 19.6 | 19.7 | 19.4 | 19.6 | 0.786 | 4.010 | 0.076 | 0.388 | NSL |
| 4 | 551 | 19.4 | 20 | 19.7 | 19.6 | 0.819 | 4.179 | 0.081 | 0.413 | NSL |
| 5 | 552 | 19.2 | 19.9 | 19.6 | 19.6 | 0.919 | 4.689 | 0.079 | 0.403 | NSL |
| Mean | | 19.250 | 19.700 | 19.460 | 19.620 | 0.840 | 4.279 | 0.080 | 0.407 | |
| SE | | 0.112 | 0.114 | 0.081 | 0.049 | 0.024 | 0.117 | 0.002 | 0.008 | |
| HDGFX (5 mg/kg) | | | | | | | | | | |
| 1 | 558 | 18.85 | 18.4 | 18.5 | 18.7 | 0.84 | 4.492 | 0.111 | 0.594 | NSL |
| 2 | 559 | 20.5 | 19.3 | 19.6 | 19.8 | 0.934 | 4.717 | 0.145 | 0.732 | NSL |
| 3 | 560 | 20.1 | 19.2 | 19.7 | 19.1 | 0.969 | 5.073 | 0.149 | 0.780 | NSL |

TABLE 5-continued

| Animals # | BP # | 3/1/00 Body WT grams | 3/3/00 Body WT | 3/5/00 Body WT | 3/8/00 Final WT grams | Liver Weight grams | Rel. Liv. Wt. gr/100 gr | Spleen Weight grams | Rel. Spl. Wt. gr/100 gr | Comments/ Gross observations |
|---|---|---|---|---|---|---|---|---|---|---|
| 4 | 561 | 21 | 19.9 | 20.6 | 20.7 | 0.957 | 4.623 | 0.116 | 0.560 | NSL |
| 5 | 562 | 18.1 | 18.1 | 18.3 | 19.8 | 0.939 | 4.742 | 0.148 | 0.747 | NSL |
| Mean | | 19.710 | 18.980 | 19.340 | 19.620 | 0.928 | 4.730 | 0.134 | 0.683 | |
| SE | | 0.537 | 0.325 | 0.423 | 0.343 | 0.023 | 0.096 | 0.008 | 0.044 | |
| | | | | | | $p < 0.05$ | $p < 0.05$ | $p < 0.01$ | $p < 0.01$ | |

* Diffuse mineralization of the heart
NSL No significant lesions

Example 8

Proliferative Activity of HDGFX

The results in Example 7 suggest that HDGFX affects the growth of pancreatic duct epithelium. Therefore the proliferative effect of HDGFX was assessed on cell cultures of these cells.

A. Demonstration of Cell Proliferation

The proliferative effect of HDGFX on H6c7 human pancreatic duct epithelial (HPDE) cells, obtained from fresh surgical samples of pancreas, was examined. Secreted HDGFX was purified from the conditioned medium described in Example 3.

Day 1: HPDE cells were plated at ~10,000/well in 6-well Nunc Tissue Culture plates in KSF medium (a keratinocyte growth supporting medium) supplemented with bovine pituitary extract and epidermal growth factor (EGF) (5 ng/ml).

Day 2: The medium was changed to KSF without supplement

Day 3: The medium was changed to KSF medium supplemented with HDGF (EXTRACT; 0.5–5 ul/ml medium), MOCK (1 and 5 ul/ml) or purified HDGF (ng/ml). Cell number at this time is ~$1.07 \times 10^4$/well. HDGF EXTRACT is a designation for minimally purified conditioned medium containing HDGFX, and MOCK relates to a control conditioned medium.

Day 7: The number of cells was counted using a Coulter ZM cell counter.

Figure 5:
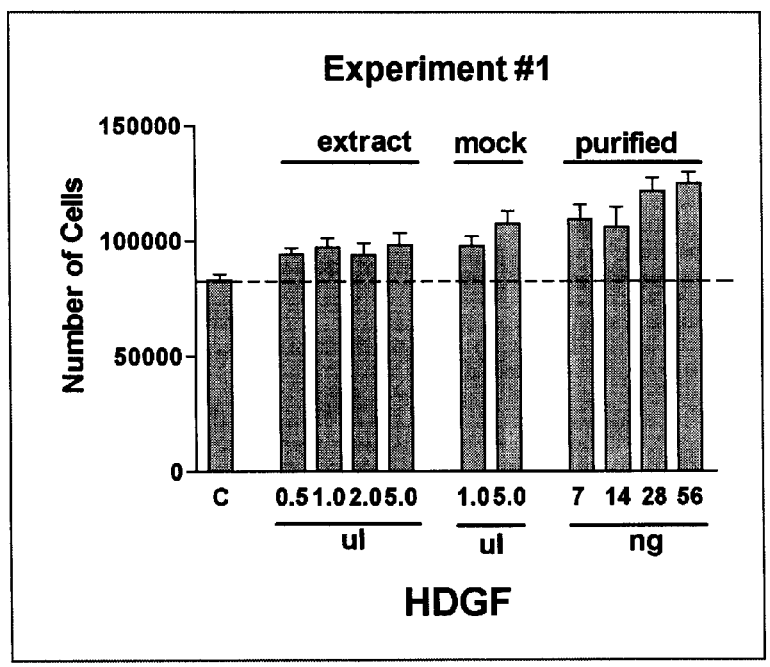
FIG. 5. Proliferation of human pancreatic duct epithelial cells in response to treatment with HDGFX.

The results are shown in FIG. 5, where HDGFX is designated HDGF. The extract effects in FIG. 5 appear to originate with the conditioned medium, and not HDGFX, since mock doses provide the same effect. HDGFX purified using the fused purification tags (Example 3) provides a significant proliferative effect (FIG. 5).

B. Suppression of Proliferation at High Concentrations of HDGF

The experiment in section A was extended by using higher concentrations of HDGF. All groups are in triplicates.

Day 1: H6c7 cells (P28) were plated in 6 well plates at ~10,000 cells/well in KSF medium without growth factor supplements.

Day 2: The medium was refreshed with the same supplement-free KSF medium.

Day 3: The medium was exchanged to medium containing various concentrations of purified HDGF. No HDGF was added to the control group.

Figure 6:
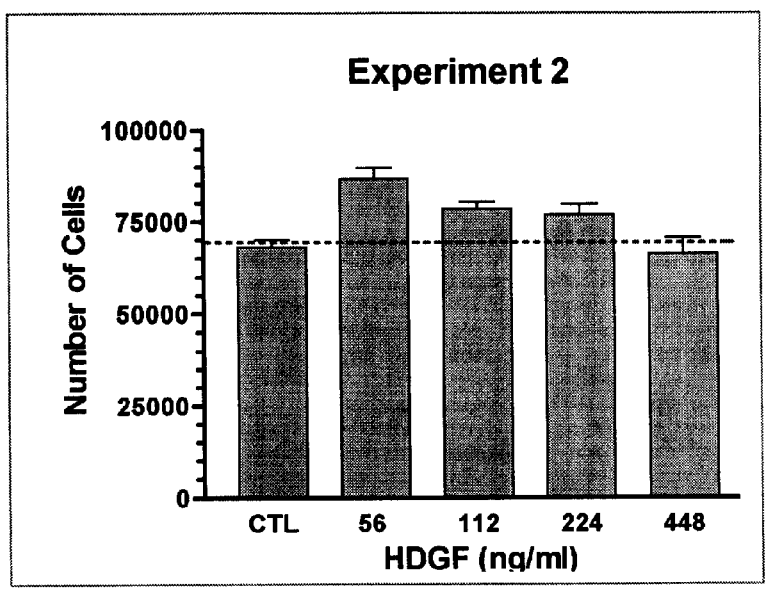
FIG. 6. Proliferation of human pancreatic duct epithelial cells in response to treatment with HDGFX.

Day 8: The cells were counted as above. The results are presented in FIG. 6.

It is seen that the lowest concentration, which is the same as the highest concentration used in part A (FIG. 5) also provides a moderate degree of proliferation. Progressively higher concentrations of HDGF appear to suppress this proliferation.

This experiment was repeated twice. In the first experiment the proliferation over control levels and suppression at high concentrations of HDGF was not found. It is believed this was due to loss of response by the cells upon repeated cell passages. In the second experiment, a proliferation to the extent of approximately 10% was observed at HDGF concentrations of 56 and 112 ng/ml, with 28 and 224 ng/ml concentrations providing a cell count indistinguishable from control (~180,000/well), and 14 ng/ml having a cell count slightly below control. The cell count in the presence of bovine pituitary extract and EGF was about 270,000/well.

Example 9

Northern Blot Analysis of Early Gene Expression by HDGFX

Figure 7:
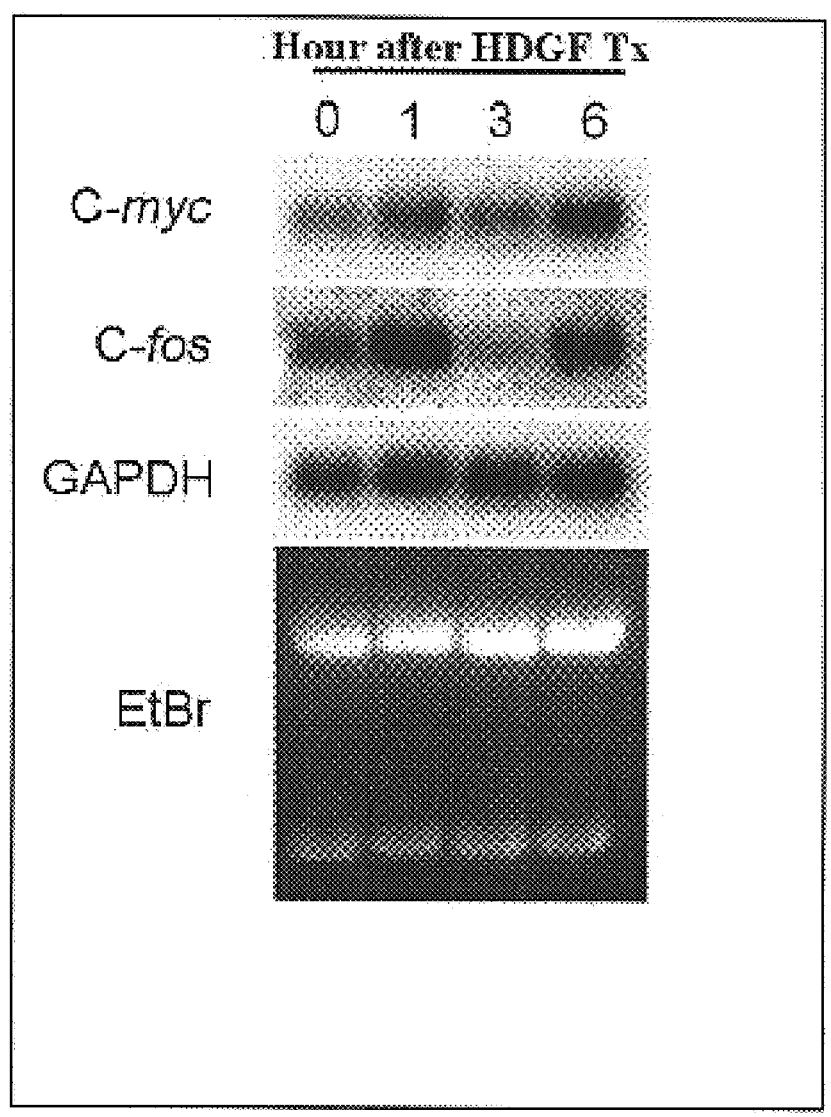
FIG. 7. Northern blot analysis of c-myc and c-fos genes in human pancreatic duct epithelial cells treated with HDGFX.

Northern blot analysis of c-myc and c-fos expression was conducted on samples of HPDE cells after treating them with HDGF (350 ng/ml) for various time periods. The results are shown in FIG. 7.

There appears to be upregulation of c-myc and c-fos mRNA expression following treatment with HDGF, compared to the constitutive expressioP of GADPH at all time points. This is consistent with activation of transcription early genes, characteristic of c-myc and c-fos, by HDGF.

Example 10

Quantitative Expression Analysis of HDGFX Nucleic Acids

The quantitative expression of variousclones was assessed in 40 normal and 54 tumor samples by real time quantitative PCR (TAQMAN®) performed on a Perkin-Elmer Biosystems ABI PRISM® 7700 Sequence Detection System. Cell lines are shown in TABLE

TABLE 4

TISSUES ANALYZED FOR HDGFX EXPRESSION

| well # | TISSUE |
|---|---|
| 1 | Endothelial cells |
| 2 | Endothelial cells (treated) |
| 3 | Pancreas |
| 4 | Pancreatic cancer CAPAN 2 |
| 5 | Adipose |
| 6 | Adrenal gland |
| 7 | Thyroid |

TABLE 4-continued

TISSUES ANALYZED FOR HDGFX EXPRESSION

| well # | TISSUE |
| --- | --- |
| 8 | Salavary gland |
| 9 | Pituitary gland |
| 10 | Brain (fetal) |
| 11 | Brain (whole) |
| 12 | Brain (amygdala) |
| 13 | Brain (cerebellum) |
| 14 | Brain (hippocampus) |
| 15 | Brain (hypothalamus) |
| 16 | Brain (substantia nigra) |
| 17 | Brain (thalamus) |
| 18 | Spinal cord |
| 19 | CNS cancer (glio/astro) U87-MG |
| 20 | CNS cancer (glio/astro) U-118-MG |
| 21 | CNS cancer (astro) SW1783 |
| 22 | CNS cancer* (neuro; met) SK-N-AS |
| 23 | CNS cancer (astro) SF-539 |
| 24 | CNS cancer (astro) SNB-75 |
| 25 | CNS cancer (glio) SNB-19 |
| 26 | CNS cancer (glio) U251 |
| 27 | CNS cancer (glio) SF-295 |
| 28 | Heart |
| 29 | Skeletal muscle |
| 30 | Bone marrow |
| 31 | Thymus |
| 32 | Spleen |
| 33 | Lymph node |
| 34 | Colon (ascending) |
| 35 | Stomach |
| 36 | Small intestine |
| 37 | Colon cancer SW480 |
| 38 | Colon cancer* (SW480 met)SW620 |
| 39 | Colon cancer HT29 |
| 40 | Colon cancer HCT-116 |
| 41 | Colon cancer CaCo-2 |
| 42 | Colon cancer HCT-15 |
| 43 | Colon cancer HCC-2998 |
| 44 | Gastric cancer* (liver met) NCI-N87 |
| 45 | Bladder |
| 46 | Trachea |
| 47 | Kidney |
| 48 | Kidney (fetal) |
| 49 | Renal cancer 786-0 |
| 50 | Renal cancer A498 |
| 51 | Renal cancer RXF 393 |
| 52 | Renal cancer ACHN |
| 53 | Renal cancer UO-31 |
| 54 | Renal cancer TK-10 |
| 55 | Liver |
| 56 | Liver (fetal) |
| 57 | Liver cancer (hepatoblast) HepG2 |
| 58 | Lung |
| 59 | Lung (fetal) |
| 60 | Lung cancer (small cell) LX-1 |
| 61 | Lung cancer (small cell) NCI-H69 |
| 62 | Lung cancer (small cell variant) SHP-77 |
| 63 | Lung cancer (large cell) NCI-H460 |
| 64 | Lung cancer (non-small cell) A549 |
| 65 | Lung cancer (non-small cell) NCI-H23 |
| 66 | Lung cancer (non-small cell) HOP-62 |
| 67 | Lung cancer (non-small cell) NCI-H522 |
| 68 | Lung cancer (squamous cell) SW 900 |
| 69 | Lung cancer (squamous cell) NCI-H596 |
| 70 | Mammary gland |
| 71 | Breast cancer* (plural. effusion) MCF-7 |
| 72 | Breast cancer* (plural effusion) MDA-MB-231 |
| 73 | Breast cancer* (plural effusion) T47D |
| 74 | Breast cancer BT-549 |
| 75 | Breast cancer MDA-N |
| 76 | Ovary |
| 77 | Ovarian cancer OVCAR-3 |
| 78 | Ovarian cancer OVCAR-4 |
| 79 | Ovarian cancer OVCAR-5 |
| 80 | Ovarian cancer OVCAR-8 |
| 81 | Ovarian cancer IGROV-1 |
| 82 | Ovarian cancer* (ascites) SK-OV-3 |
| 83 | Myometrium |
| 84 | Uterus |
| 85 | Plancenta |
| 86 | Prostate |
| 87 | Prostate cancer* (bone met)PC-3 |
| 88 | Testis |
| 89 | Melanoma Hs688(A).T |
| 90 | Melanoma* (met) Hs688(B).T |
| 91 | Melanoma UACC-62 |
| 92 | Melanoma M14 |
| 93 | Melanoma LOX IMVI |
| 94 | Melanoma* (met) SK-MEL-5 |
| 95 | Melanoma SK-MEL-28 |
| 96 | Melanoma UACC-257 |

*KEY: glio. = gliocyte; astro. = astrocyte; neuro. = neurocyte; met. = metastatic; CNS = central nervous system First, 96 RNA samples were normalized to β-actin and GAPDH. RNA (~50 ng total or ~1 ng polyA+) was converted to cDNA using the TAQMAN® Reverse Transcription Reagents Kit (PE Biosystems, Foster City, Calif.; cat # N8080234) and random hexamers according to the manufacturer's protocol. Reactions were performed in 20 ul and incubated for 30 min. at 48° C. cDNA (5 ul) was then transferred to a separate plate for the TAQMAN® reaction using β-actin and GAPDH TAQMAN® Assay Reagents (PE Biosystems; cat. #'s 4310881E and 4310884E, respectively) and TAQMAN® universal PCR Master Mix (PE Biosystems; cat # 4304447) according to the manufacturer's protocol. Reactions were performed in 25 ul using the following parameters: 2 min. at 50° C.; 10 min. at 95° C.; 15 sec. at 95° C./1 min. at 60° C. (40 cycles). Results were recorded as CT values (cycle at which a given sample crosses a threshold level of flourescence) using a log scale, with the difference in RNA concentration between a given sample and the sample with the lowest CT value being represented as 2 to the power of delta CT. The percent relative expression is then obtained by taking the reciprocal of this RNA difference and multiplying by 100. The average CT values obtained for β-actin and GAPDH were used to normalize RNA samples. The RNA sample generating the highest CT value required no further diluting, while all other samples were diluted relative to this sample according to their —average CT values.

Normalized RNA (5 ul) was converted to cDNA and analyzed via TAQMAN® using One step RT-PCR Master Mix Reagents (PE Biosystems; cat. # 4309169) and gene-specific primers according to the manufacturer's instructions. Probes and primers were designed for each assay according to Perkin Elmer Biosystem's Primer Express Software package (version I for Apple Computer's Macintosh Power PC) using the sequence of clone HDGFX_A as input. Default settings were used for reaction conditions and the following parameters were set before selecting primers: primer concentration=250 nM, primer melting temperature ($T_m$) range=58°–60° C., primer optimal Tm=59° C., maximum primer difference=2° C., probe does not have 5'G, probe $T_m$ must be 10° C. greater than primer $T_m$, amplicon size 75 bp to 100 bp. The probes and primers selected (see below) were synthesized by Synthegen (Houston, Tex., USA). Probes were double purified by HPLC to remove uncoupled dye and evaluated by mass spectroscopy to verify coupling of reporter and quencher dyes to the 5' and 3' ends of the probe, respectively. Their final concentrations were: forward and reverse primers, 900 nM each, and probe, 200 nM.

PCR conditions: Normalized RNA from each tissue and each cell line was spotted in each well of a 96 well PCR plate (Perkin Elmer Biosystems). PCR cocktails including two probes (HDGFX_A-specific and another gene-specific probe multiplexed with the HDGFX_A probe) were set up using 1×TaqMan™ PCR Master Mix for the PE Biosystems 7700, with 5 mM MgCl2, dNTPs (dA, G, C, U at 1:1:1:2 ratios), 0.25 U/ml AmpliTaq Gold™ (PE Biosystems), and 0.4 U/μl RNase inhibitor, and 0.25 U/μl reverse transcriptase. Reverse transcription was performed at 48° C. for 30 minutes followed by amplification/PCR cycles as follows: 95° C. 10 min, then 40 cycles of 95° C. for 15 seconds, 60° C. for 1 minute.

A. Probe Set Ag082b

| Primers | Sequences | nt | Start Position | SEQ ID NO: |
|---|---|---|---|---|
| Forward | 5'-ACCAGGTGTTTTTCTTCGGGA-3' | 21 | 191 | 17 |
| Probe | FAM-5'-CCACGAGACGGCCTTCCTGA-GTCC-3'-TAMRA | 24 | 213 | 18 |
| Reverse | 5'-TTGTACGGGAACAGGCGTTT-3' | 20 | 238 | 19 |

Expression of clone HDGFX_A is detected by primer-probe set Ag082b only in normal testis (100.0% relative expression) and pancreas (9.0% relative expression), of all the normal and cancer tissues assayed.

B. Probe Set Ag082c

| Primers | Sequences | SEQ ID NO: |
|---|---|---|
| Forward | 5'- ACCAGGTGTTTTTCTTCGGGA -3' | 20 |
| Probe | FAM-CCACGAGACGGCCTTCCTGAGTCC-TAMRA | 21 |
| Reverse | 5'- TTGTACGGGAACAGGCGTTT -3' | 22 |

Expression of clone HDGFX_A is detected by primer-probe set Ag082c only in normal testis (100.0% relative expression) and pancreas (9.7% relative expression), of all the normal and cancer tissues assayed.

EQUIVALENTS

From the foregoing detailed description of the specific embodiments of the invention, it should be apparent that particular novel compositions and methods involving nucleic acids, polypeptides, antibodies, detection and treatment have been described. Although these particular embodiments have been disclosed herein in detail, this has been done by way of example for purposes of illustration only, and is not intended to be-limiting with respect to the scope of the appended claims that follow. In particular, it is contemplated by the inventors that various substitutions, alterations, and modifications may be made as a matter of routine for a person of ordinary skill in the art to the invention without departing from the spirit and scope of the invention as defined by the claims. Indeed, various modifications of the invention in addition to those described herein will become apparent to those skilled in the art from the foregoing description and accompanying figures. Such modifications are intended to fall within the scope of the appended claims.

What is claimed is:

1. A composition comprising a polypeptide that comprises the amino acid sequence of SEQ ID NO:2 and a pharmaceutically acceptable carrier.

2. A kit comprising in one or more containers, the composition of claim 1.

3. An isolated polypeptide comprising the amino acid sequence of SEQ ID NO:2.

4. An isolated polypeptide consisting of the amino acid sequence of SEQ ID NO:2.

5. An isolated polypeptide comprising an amino acid sequence that is at least 99% identical to the amino acid sequence of SEQ ID NO:2, wherein the polypeptide has an activity selected from the group consisting of:
   (a) a fibroblast growth factor activity; and
   (b) a cell proliferative activity.

6. An isolated polypeptide comprising a mature form of the amino acid sequence of SEQ ID NO:2.

* * * * *